(12) United States Patent  (10) Patent No.: US 7,732,039 B2
Chakravarty et al.  (45) Date of Patent: Jun. 8, 2010

(54) ABSORBENT ARTICLE WITH STABILIZED ABSORBENT STRUCTURE HAVING NON-UNIFORM LATERAL COMPRESSION STIFFNESS

(75) Inventors: Jayant Chakravarty, Appleton, WI (US); Mark J. Beitz, Appleton, WI (US); David L. Zenker, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1275 days.

(21) Appl. No.: 10/306,277

(22) Filed: Nov. 27, 2002

(65) Prior Publication Data

US 2003/0119401 A1 Jun. 26, 2003

Related U.S. Application Data

(63) Continuation-in-part of application No. 10/033,860, filed on Dec. 20, 2001, now abandoned.

(51) Int. Cl.
*A61F 13/15* (2006.01)
(52) U.S. Cl. ............... 428/174; 428/213; 428/218; 604/379; 604/380; 604/385.01
(58) Field of Classification Search ........... 428/174, 428/213, 218; 604/379, 380, 385.01
See application file for complete search history.

(56) References Cited

U.S. PATENT DOCUMENTS

| | | | |
|---|---|---|---|
| 3,759,775 A | 9/1973 | Shepherd |
| 3,802,817 A | 4/1974 | Matsuki, at al. |
| 3,803,453 A | 4/1974 | Hull |
| 3,849,241 A | 11/1974 | Butin et al. |
| 3,860,002 A | 1/1975 | Kolbach |
| 3,901,236 A | 8/1975 | Assarsson et al. |
| 4,016,628 A | 4/1977 | Kolbach |
| 4,076,663 A | 2/1978 | Masuda et al. |
| 4,100,324 A | 7/1978 | Anderson et al. |

(Continued)

FOREIGN PATENT DOCUMENTS

DE 40 24 053 A1 1/1992

(Continued)

OTHER PUBLICATIONS

Patent Abstracts of Japan 06038814 B4: Description of Igaue Takamitsu, et al., "Absorbing Body for Absorbable Article and Preparation Thereof", Mar. 1990.

(Continued)

*Primary Examiner*—Elizabeth M Cole
(74) *Attorney, Agent, or Firm*—Armstrong Teasdale, LLP

(57) ABSTRACT

An absorbent article having a liner adapted for contiguous relationship with the wearer's body, an outer cover in generally opposed relationship with the liner, and an absorbent body disposed between the liner and the outer cover. An absorbent structure of the absorbent body has a length, a thickness, a width, a longitudinal axis and a non-uniform lateral compression stiffness across its width. The non-uniform lateral compression stiffness is such that the absorbent structure assumes a pre-determined, or non-random buckled configuration under lateral compression thereof. In one embodiment, the buckled configuration is generally symmetric about a plane normal to the absorbent structure and in which the longitudinal axis of the absorbent structure lies.

33 Claims, 18 Drawing Sheets

U.S. PATENT DOCUMENTS

| | | |
|---|---|---|
| RE29,789 E | 10/1978 | Kolbach |
| 4,186,165 A | 1/1980 | Aberson et al. |
| 4,286,082 A | 8/1981 | Tsubakimoto et al. |
| 4,297,410 A | 10/1981 | Tsuchiya et al. |
| 4,309,479 A | 1/1982 | Naruse et al. |
| 4,340,563 A | 7/1982 | Appel et al. |
| 4,375,448 A | 3/1983 | Appel et al. |
| 4,392,908 A | 7/1983 | Dehnel |
| 4,401,708 A | 8/1983 | Paul |
| 4,429,001 A | 1/1984 | Kolpin et al. |
| 4,494,278 A | 1/1985 | Kroyer et al. |
| 4,530,353 A | 7/1985 | Lauritzen |
| 4,542,199 A | 9/1985 | Kaminsky et al. |
| 4,631,062 A | 12/1986 | Lassen et al. |
| 4,640,810 A | 2/1987 | Laursen et al. |
| 4,663,220 A | 5/1987 | Wisneski et al. |
| 4,666,647 A | 5/1987 | Enloe et al. |
| 4,674,966 A | 6/1987 | Johnson et al. |
| 4,704,116 A | 11/1987 | Enloe |
| 4,721,647 A | 1/1988 | Nakanishi et al. |
| 4,725,448 A | 2/1988 | Fitzpatrick |
| 4,743,505 A | 5/1988 | Yamada et al. |
| 4,755,178 A | 7/1988 | Insley et al. |
| 4,756,969 A | 7/1988 | Takeda |
| 4,761,258 A | 8/1988 | Enloe et al. |
| 4,767,825 A | 8/1988 | Pazos et al. |
| 4,786,915 A | 11/1988 | Cartwright et al. |
| 4,795,668 A | 1/1989 | Krueger et al. |
| 4,798,603 A | 1/1989 | Meyer et al. |
| 4,813,948 A | 3/1989 | Insley |
| 4,818,315 A | 4/1989 | Hellgren et al. |
| 4,818,464 A | 4/1989 | Lau |
| 4,921,645 A | 5/1990 | Insley |
| 4,927,582 A | 5/1990 | Bryson |
| 4,939,016 A | 7/1990 | Radwanski et al. |
| 5,002,814 A | 3/1991 | Knack et al. |
| 5,057,368 A | 10/1991 | Largman et al. |
| 5,064,802 A | 11/1991 | Stevens et al. |
| 5,069,970 A | 12/1991 | Largman et al. |
| 5,108,820 A | 4/1992 | Kaneko et al. |
| 5,108,827 A | 4/1992 | Gessner |
| 5,139,861 A | 8/1992 | Williams et al. |
| 5,143,680 A | 9/1992 | Molnar et al. |
| 5,147,343 A | 9/1992 | Kellenberger |
| 5,148,172 A | 9/1992 | Kumurdjian |
| 5,155,316 A | 10/1992 | Chiu |
| 5,176,668 A | 1/1993 | Bernardin |
| 5,176,672 A | 1/1993 | Bruemmer et al. |
| 5,185,506 A | 2/1993 | Walters |
| 5,188,624 A | 2/1993 | Young, Sr. et al. |
| 5,192,606 A | 3/1993 | Proxmire et al. |
| 5,217,768 A | 6/1993 | Walters et al. |
| 5,220,143 A | 6/1993 | Kemske et al. |
| 5,226,992 A | 7/1993 | Morman |
| 5,230,959 A | 7/1993 | Young, Sr. et al. |
| 5,246,770 A | 9/1993 | Bottiglione et al. |
| 5,254,821 A | 10/1993 | Walters |
| 5,277,976 A | 1/1994 | Hogle et al. |
| 5,294,482 A | 3/1994 | Gessner |
| 5,300,055 A | 4/1994 | Buell |
| 5,304,161 A | 4/1994 | Noel et al. |
| 5,318,650 A | 6/1994 | Kerawalla |
| 5,334,446 A | 8/1994 | Quantrille et al. |
| 5,336,552 A | 8/1994 | Strack et al. |
| 5,350,904 A | 9/1994 | Kemske et al. |
| 5,368,918 A | 11/1994 | Harada et al. |
| 5,374,696 A | 12/1994 | Rosen et al. |
| 5,382,400 A | 1/1995 | Pike et al. |
| 5,393,599 A | 2/1995 | Quantrille et al. |
| 5,418,045 A | 5/1995 | Pike et al. |
| 5,431,991 A | 7/1995 | Quantrille et al. |
| 5,436,066 A | 7/1995 | Chen |
| 5,466,409 A | 11/1995 | Partridge et al. |
| 5,466,410 A | 11/1995 | Hills |
| 5,486,166 A | 1/1996 | Bishop et al. |
| 5,489,469 A | 2/1996 | Kobayashi et al. |
| 5,490,846 A | 2/1996 | Ellis et al. |
| 5,492,754 A | 2/1996 | Chen |
| 5,496,298 A | 3/1996 | Kuepper et al. |
| 5,509,915 A | 4/1996 | Hanson et al. |
| 5,516,585 A | 5/1996 | Young, Sr. et al. |
| 5,527,171 A | 6/1996 | Soerensen |
| 5,536,921 A | 7/1996 | Hedrick et al. |
| 5,540,796 A | 7/1996 | Fries |
| 5,540,992 A | 7/1996 | Marcher et al. |
| 5,562,646 A | 10/1996 | Goldman et al. |
| 5,567,744 A | 10/1996 | Nagata et al. |
| 5,585,170 A | 12/1996 | Morris et al. |
| 5,595,618 A | 1/1997 | Fries et al. |
| 5,599,334 A | 2/1997 | Johnston et al. |
| 5,599,763 A | 2/1997 | Harada et al. |
| 5,601,542 A | 2/1997 | Melius et al. |
| 5,601,544 A | 2/1997 | Glaug et al. |
| 5,607,415 A | 3/1997 | Datta et al. |
| 5,651,778 A | 7/1997 | Melius et al. |
| 5,672,419 A | 9/1997 | Mukaida et al. |
| 5,674,339 A | 10/1997 | Groeger et al. |
| 5,722,967 A | 3/1998 | Coles |
| 5,766,213 A | 6/1998 | Hackman et al. |
| 5,786,785 A | 7/1998 | Gindrup et al. |
| 5,800,418 A | 9/1998 | Ahr |
| 5,858,515 A | 1/1999 | Stokes et al. |
| 5,858,535 A | 1/1999 | Wang et al. |
| 5,885,516 A | 3/1999 | Christensen et al. |
| 5,916,203 A | 6/1999 | Brandon et al. |
| 5,916,506 A | 6/1999 | Breznak et al. |
| 5,961,509 A | 10/1999 | Kling |
| 5,962,108 A | 10/1999 | Nestegard et al. |
| 5,972,808 A | 10/1999 | Groeger et al. |
| 5,981,410 A | 11/1999 | Hansen et al. |
| 5,993,433 A | 11/1999 | St. Louis et al. |
| 5,994,615 A | 11/1999 | Dodge, II et al. |
| 6,004,422 A | 12/1999 | Janovec et al. |
| 6,024,813 A | 2/2000 | Groeger et al. |
| 6,024,822 A | 2/2000 | Alper et al. |
| 6,078,035 A | 6/2000 | Chittipeddi et al. |
| 6,140,550 A | 10/2000 | Beihoffer et al. |
| H1909 H | 11/2000 | Ahr |
| 6,160,197 A | 12/2000 | Lassen et al. |
| 6,214,274 B1 | 4/2001 | Melius et al. |
| 6,239,230 B1 | 5/2001 | Eckert et al. |
| 6,242,094 B1 | 6/2001 | Breznak et al. |
| 6,248,097 B1 | 6/2001 | Beitz et al. |
| 6,312,416 B1 | 11/2001 | Brisebois |
| 6,323,388 B1 | 11/2001 | Melius et al. |
| 6,328,779 B1 | 12/2001 | He et al. |
| 6,330,735 B1 | 12/2001 | Hahn et al. |
| 6,376,011 B1 | 4/2002 | Reeves et al. |
| 6,413,634 B1 | 7/2002 | Tanaka et al. |
| 6,419,798 B1 | 7/2002 | Topolkaraev et al. |
| 6,447,494 B1 | 9/2002 | Kashiwagi et al. |
| 6,495,656 B1 | 12/2002 | Haile et al. |
| 6,533,987 B2 | 3/2003 | Topolkaraev et al. |
| 6,562,938 B2 | 5/2003 | Haile et al. |
| 6,593,255 B1 | 7/2003 | Lawton et al. |
| 6,617,490 B1 | 9/2003 | Chen et al. |
| 6,766,817 B2 | 7/2004 | da Silva |
| 2002/0115977 A1 | 8/2002 | Topolkaraev et al. |
| 2002/0135103 A1 | 9/2002 | Odorzynski et al. |
| 2002/0150761 A1 | 10/2002 | Lange et al. |
| 2003/0116888 A1 | 6/2003 | Rymer et al. |
| 2003/0116890 A1 | 6/2003 | Chambers, Jr. et al. |
| 2003/0118814 A1 | 6/2003 | Workman, Jr. et al. |
| 2003/0118825 A1 | 6/2003 | Melius et al. |

| | | | |
|---|---|---|---|
| 2003/0119394 A1 | 6/2003 | Ranganathan et al. | |
| 2003/0119400 A1 | 6/2003 | Beitz et al. | |
| 2003/0119401 A1 | 6/2003 | Chakravarty et al. | |
| 2003/0119402 A1 | 6/2003 | Melius et al. | |
| 2003/0119405 A1 | 6/2003 | Abuto et al. | |
| 2003/0119406 A1 | 6/2003 | Abuto et al. | |
| 2003/0119413 A1 | 6/2003 | Chakravarty et al. | |
| 2003/0129392 A1 | 7/2003 | Abuto et al. | |
| 2004/0237529 A1 | 12/2004 | da Silva | |

FOREIGN PATENT DOCUMENTS

| | | |
|---|---|---|
| EP | 0 217 032 B1 | 4/1987 |
| EP | 0 345 523 A1 | 12/1989 |
| EP | 0 479 422 A1 | 4/1992 |
| EP | 0 479 442 A1 | 4/1992 |
| EP | 0 509 708 A1 | 10/1992 |
| EP | 0 525 778 A2 | 2/1993 |
| EP | 0 533 982 A1 | 3/1993 |
| EP | 0 540 041 A1 | 5/1993 |
| EP | 0 625 602 A1 | 11/1994 |
| EP | 0 627 211 A1 | 12/1994 |
| EP | 0 649 644 B1 | 4/1995 |
| EP | 0 665 315 B1 | 8/1995 |
| EP | 687453 A1 | 12/1995 |
| EP | 0 842 650 A1 | 5/1998 |
| EP | 0 916 328 A1 | 12/1998 |
| EP | 1 029 886 A2 | 8/2000 |
| EP | 1 145 724 A1 | 10/2001 |
| EP | 1 160 426 A2 | 12/2001 |
| GB | 1071191 | 6/1967 |
| GB | 1 092 373 | 11/1967 |
| GB | 2 196 343 A | 4/1988 |
| GB | 2 301 350 A | 6/1996 |
| WO | WO 89/11772 A1 | 12/1989 |
| WO | WO 90/11171 A1 | 10/1990 |
| WO | WO 91/18042 A1 | 11/1991 |
| WO | WO 91/19036 A1 | 12/1991 |
| WO | WO 95/31165 A1 | 11/1995 |
| WO | WO 96/14885 A1 | 5/1996 |
| WO | WO 97/27884 A1 | 8/1997 |
| WO | WO 98/48857 A1 | 11/1998 |
| WO | WO 99/16399 A1 | 4/1999 |
| WO | WO 99/22685 A1 | 5/1999 |
| WO | WO 99/63923 A1 | 12/1999 |
| WO | WO 00/19956 A1 | 4/2000 |
| WO | WO 00/29657 A1 | 5/2000 |
| WO | WO 99/29655 A1 | 5/2000 |
| WO | WO 00/31331 A1 | 6/2000 |
| WO | WO 00/37002 A1 | 6/2000 |
| WO | WO 00/59439 A1 | 10/2000 |
| WO | WO 00/62825 A2 | 10/2000 |
| WO | WO 00/62922 A1 | 10/2000 |
| WO | WO 00/69383 A1 | 11/2000 |
| WO | WO 00/71790 A1 | 11/2000 |
| WO | WO 00/78369 A1 | 12/2000 |
| WO | WO 01/05440 A2 | 1/2001 |
| WO | WO 01/26592 A1 | 4/2001 |
| WO | WO 01/26595 A1 | 4/2001 |
| WO | WO 01/35886 A1 | 5/2001 |
| WO | WO 01/48291 A1 | 7/2001 |
| WO | WO 01/85824 A2 | 11/2001 |
| WO | WO 01/95347 A2 | 12/2001 |
| WO | WO 02/076520 A2 | 10/2002 |
| WO | WO 02/077347 A2 | 10/2002 |

OTHER PUBLICATIONS

TAPPI Official Test Method T 494 om-96, "Tensile Properties of Paper and Paperboard (Using Constant Rate of Elongation Apparatus)," published by the TAPPI Press Atlanta, Georgie, revised 1996, pp. 1-10.

International Search Report for PCT/US 02/40778 dated Apr. 10, 2003, 9 pages.

Derwent Abstract; XP 002240776 and JP 58 019360 A; Feb. 4, 1983.

Derwent Abstract; XP 002240768 and JP 61 055249 A; Mar. 19, 1986.

Derwent Abstract; XP 002240906 and KR 8 901 835 B; May 25, 1989.

Patent Abstracts of Japan; Jan. 21, 1994 and JP 05 263318 A; Oct. 12, 1993.

International Search Report for PCT/US 02/40779 dated Aug. 28, 2003.

American Society for Testing Materials (ASTM) Designation: D1921-89, "Standard Test Methods for Particle Size (Sieve Analysis) of Plastic Materials,"pp. 493-496, published Aug. 1989.

TAPPI Official Test Method T494 om-96, "Tensile Properties of Paper and Paperboard," published by the TAPPI Press, Atlanta, Georgia, revised 1996, pp. 1-10.

*Polymer Blends and Composites*, John A. Manson and Leslie H. Sperling, 1976, Plenum Press, New York, pp. 273-277.

Microwave Processing of Materials, Publication NMAB-473, National Academy Press, Washington, DC, 1994.

"Reversible Microwave Bonding," Oak Ridge National Laboratory, Mar. 24, 2000, www.oml.gov/orccmt/pages/projects.html.

"Radio-Frequency Sealing or Disposable Medical Products," Medical Devicelink.com, Mar. 24, 2000, www.devicelink.com/mddl/archive/99/12/003.html.

*Industrial Microwave Heating*, A. C. Metaxas & R. J. Meredith, Peter Peregrinus Ltd., London, England, 1983, p. 152.

Svensk, Papperstidning, "A New Method for Measuring the Edgewise Compression Properties of Paper," Sören Cavlin and Christer Fellers, No. 9, 1975, pp. 328-332.

"Handbook of Physical Testing of Paper," (vol. 1—Second Edition), by R.E. Mark, C.C. Habegar, J. Borche and M.B. Lynch (ISBN:0-8247-0498-3), Sep. 2001.

International Search Report for PCT/US 02/22845 dated Nov. 11, 2002, 4 pages.

ABSORBENT ARTICLE WITH STABILIZED ABSORBENT STRUCTURE HAVING NON-UNIFORM LATERAL COMPRESSION STIFFNESS

CROSS-REFERENCE TO RELATED APPLICATIONS

This application is a continuation-in-part patent application of U.S. patent application Ser. No. 10/033,860 entitled Targeted On-Line Stabilized Absorbent Structures; which was filed on Dec. 20, 2001 now abandoned and is fully incorporated herein by reference.

BACKGROUND OF THE INVENTION

The present invention relates generally to absorbent articles, such as those used as personal care products, and more particularly to such an absorbent article having an absorbent body comprised at least in part of a stabilized non-woven absorbent structure.

Absorbent articles find widespread use as personal care products such as diapers, children's toilet training pants, adult incontinence garments, medical garments, sanitary napkins and the like, as well as surgical bandages and sponges. These articles absorb and contain body waste and are typically disposable in the sense that they are intended to be discarded after a limited period of use; i.e., the articles are not intended to be laundered or otherwise restored for reuse. Conventional disposable absorbent articles comprise an absorbent body disposed between a liner adapted for contiguous relationship with the wearer's skin and an outer cover for inhibiting liquid body waste absorbed by the absorbent body from leaking out of the article. The liner of the absorbent article is typically liquid permeable to permit liquid body waste to pass therethrough for absorption by the absorbent body.

In one general practice of forming fibrous webs (commonly referred to as airforming) for use as an absorbent body in such absorbent articles, discrete fibers such as cellulosic or other suitable absorbent fibers are introduced into an airforming device along with particulate or fibrous superabsorbent material. The absorbent fibers and superabsorbent particles are entrained in an air stream within the airforming device and directed onto a foraminous forming surface upon which the mixture of absorbent fibers and superabsorbent particles are collected to form an absorbent fibrous web or structure.

Airforming devices employed in high-speed commercial operations typically have a forming surface constructed of a wire screen or fluted grid, and one or more form members which, together with the wire screen or fluted grid, generally define the length, width and thickness profiles of the absorbent structure to be formed on the forming surface. A pneumatic flow mechanism, such as a vacuum suction system, draws the air-entrained fiber stream within the airforming device onto the forming surface, and pass the airflow through the forming surface has been employed in high-speed commercial operations. By using such an airforming device, absorbent structures have been formed with gradations in basis weight (e.g., thickness) along the length and/or width of the absorbent structure, and have also been formed to have a generally non-uniform width.

While airformed absorbent structures that comprise a mixture of absorbent fibers and superabsorbent material have proven useful in making absorbent bodies of preferred shapes and sizes for various absorbent articles, further improvement is desired. More particularly, such absorbent structures lack the structural integrity or stability to maintain its original shape (e.g., length, width and particularly thickness) following repeated liquid insults by the wearer.

To this end, it is known to use a conventional airlaying process to form a stabilized absorbent web or structure in which binder materials have been added to the structure. Such binder materials have included adhesives, powders, netting, and binder fibers. The binder fibers have included one or more of the following types of fibers: homofilaments, heat-fusible fibers, bicomponent fibers, meltblown polyethylene fibers, meltblown polypropylene fibers, and the like.

In conventional airlaying systems, binder fibers are mixed with absorbent fibers and superabsorbent materials and the mixture is then deposited onto a porous forming surface by using a vacuum system to draw the fibers onto the forming surface. The structure formed on the forming surface is then heated to activate the binder fibers whereby the binder fibers melt and form inter-fiber bonds with the absorbent fibers to form a stabilized structure.

Such conventional airlaying systems, however, have been limited with regard to the lengths of the binder fibers that can be efficiently employed. In the operation of the conventional systems, the lengths of the binder fibers have typically been 6 mm or less. Attempts to use longer binder fibers have caused plugging of distribution screens, non-uniform distribution of fibers, fiber clumping, and other basis weight uniformity problems. Such airlaying systems have also required the use of excessive amounts of energy. Where the binder fibers are heat-activated to provide the stabilized web structure, it has been necessary to subject the structure to an excessively long heating time to adequately heat the binder fibers. For instance, typical heating times with through-air bonding systems are in the range of 7-8 seconds. Additionally, it has been necessary to subject the fibrous web to an excessively long cooling time, such as during roll storage in warehouses, to establish and preserve the desired stabilized structure prior to further processing operations.

As a result, conventional airlaying systems have been inadequate for manufacturing stabilized absorbent structures directly in-line on consumer product converting machines at high-speeds. Rather, where stabilized absorbent structures are desired for use in making absorbent bodies for absorbent articles, the common approach has been to manufacture wider than needed stabilized webs off-line whereby the webs are rolled and stored for subsequent use in separate manufacturing machines.

One particular disadvantage of such an approach is that conventional airlaying systems are limited as to dimensioning of the stabilized structure formed thereby. More particularly, the stabilized structure formed by existing airlaying systems has both a uniform width (e.g., straight side edges) and a substantially uniform basis weight and thickness. Where a shaped absorbent structure having a non-uniform width is desired, such as an absorbent structure having a narrowed crotch region, the previously formed stabilized web must be unrolled and the side edges of the web must be cut to provide the desired width profile. Such cutting and shaping of the selected segments of the stabilized web results in excessive wasted amounts of the stabilized web, and has excessively complicated the manufacturing operations. In addition, conventional systems have resulted in excessive costs associated with the shipping, storage, and roll handling of the relatively low density materials.

Another disadvantage of such an approach is that when lateral compression is applied to a stabilized absorbent structure, such as by being squeezed between the legs of a wearer of an absorbent article incorporating such an absorbent structure, the uniform basis weight and density of the structure, particularly across its width, causes the structure to undesirably randomly buckle, or fold (e.g., along longitudinal fold lines) at multiple locations across the width of the structure.

Also, where a non-uniform basis weight or thickness is desired, e.g., to provide the absorbent structure with a targeted area of increased basis weight for increased absorbing capacity, a smaller (e.g., narrower) layer must be cut from one stabilized web and then overlayed and bonded onto a larger stabilized web to increase the basis weight of the absorbent structure at the targeted area. This requires additional steps and even further complicates manufacturing operations.

SUMMARY OF THE INVENTION

In general, one embodiment of an absorbent article of the present invention comprises a liner adapted for contiguous relationship with the wearer's body, an outer cover in generally opposed relationship with the liner, and an absorbent body disposed between the liner and the outer cover. The absorbent body at least partially comprises an absorbent structure having a length, a thickness, a width, a longitudinal axis and a non-uniform lateral compression stiffness across its width. The non-uniform lateral compression stiffness is such that the absorbent structure assumes a generally buckled configuration under lateral compression thereof wherein the buckled configuration is generally symmetric about a plane normal to the absorbent structure and in which the longitudinal axis of the absorbent structure lies.

In another embodiment, the absorbent article generally comprises a liner adapted for contiguous relationship with the wearer's body, an outer cover in generally opposed relationship with the liner, and an absorbent body disposed between the liner and the outer cover. The absorbent body at least partially comprises an absorbent structure having a length, a thickness, a width, a longitudinal axis and a non-uniform lateral compression stiffness across its width. The non-uniform lateral compression stiffness is such that the absorbent structure assumes a pre-determined generally buckled configuration under lateral compression thereof. In another embodiment, the absorbent article generally comprises a liner adapted for contiguous relationship with the wearer's body, an outer cover in generally opposed relationship with the liner, and an absorbent body disposed between the liner and the outer cover. The absorbent body at least partially comprises an absorbent structure having a length, a thickness, a width, a longitudinal axis and a non-uniform lateral compression stiffness across its width. The non-uniform lateral compression stiffness is such that the absorbent structure assumes a non-random, generally buckled configuration under lateral compression thereof.

BRIEF DESCRIPTION OF THE DRAWINGS

FIG. 17b is a cross-section taken in the plane of line 17b-17b of FIG. 17a;

FIG. 18b is a cross-section taken in the plane of line 18b-18b of FIG. 18a;

FIG. 19b is a cross-section taken in the plane of line 19b-19b of FIG. 19a.

Corresponding reference characters indicate corresponding parts throughout the several views of the drawings.

DETAILED DESCRIPTION OF THE PREFERRED EMBODIMENTS

Figure 1:
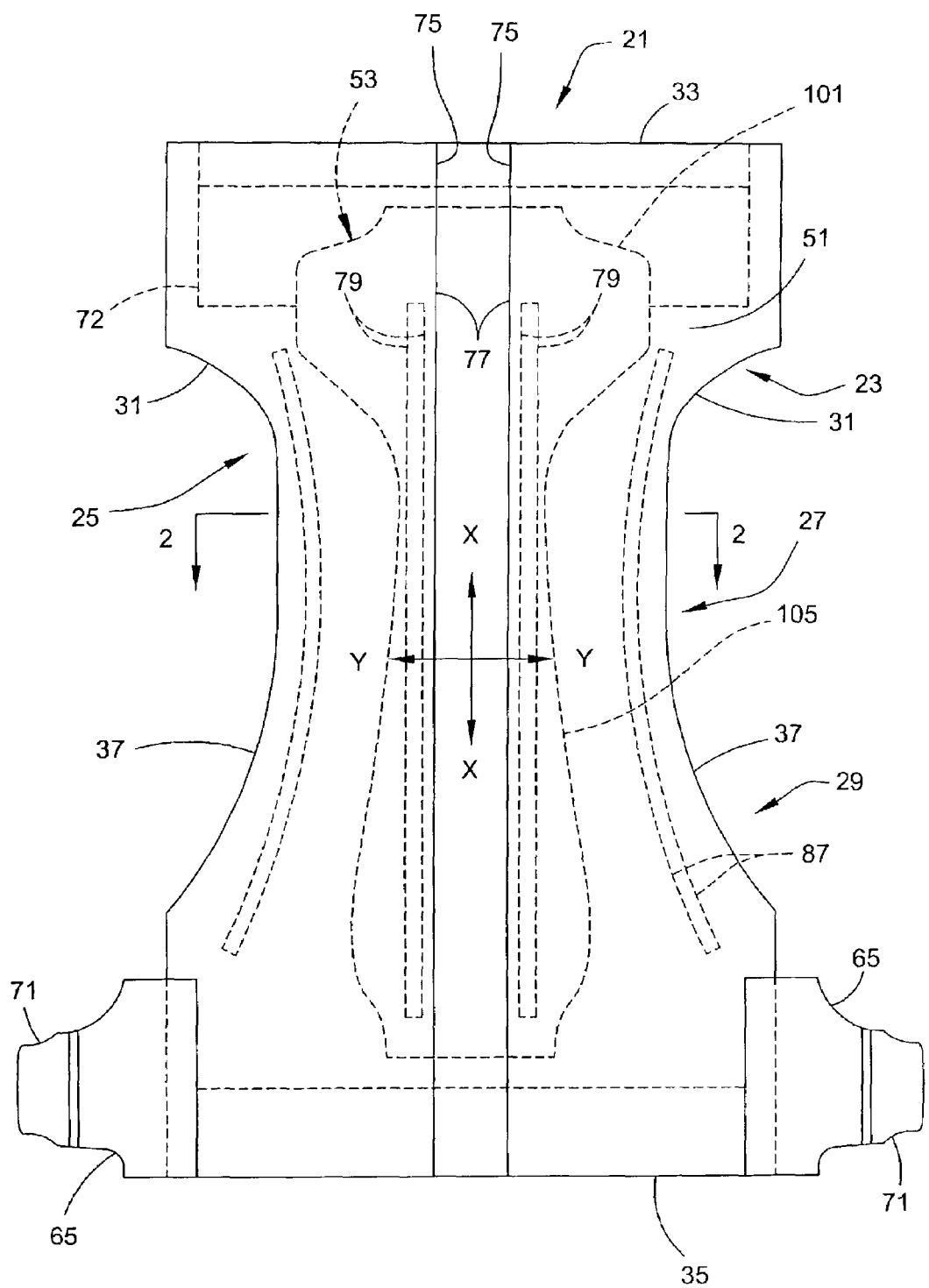
FIG. 1 is a plan view of an absorbent article of the present invention illustrated in the form of a diaper shown unfastened and laid flat.

Referring now to the drawings and in particular to FIG. 1, one example of an absorbent article constructed in accordance with the present invention is illustrated in the form of a diaper, which is indicated in its entirety by the reference numeral 21. As used herein, an absorbent article refers to an article which may be placed against or in proximity to the body of the wearer (e.g., contiguous to the body) to absorb and/or retain various waste discharged from the body. Some absorbent articles, such as disposable absorbent articles, are intended to be discarded after a limited period of use instead of being laundered or otherwise restored for reuse. It is contemplated, however, that the principles of the present invention have application in garments (including reusable garments) and other absorbent articles. For example, the principles of the present invention may be incorporated into children's training pants and other infant and child care products, adult incontinence garments and other adult care products, medical garments, sanitary napkins and other feminine care products and the like, as well as surgical bandages and sponges.

Figure 3:
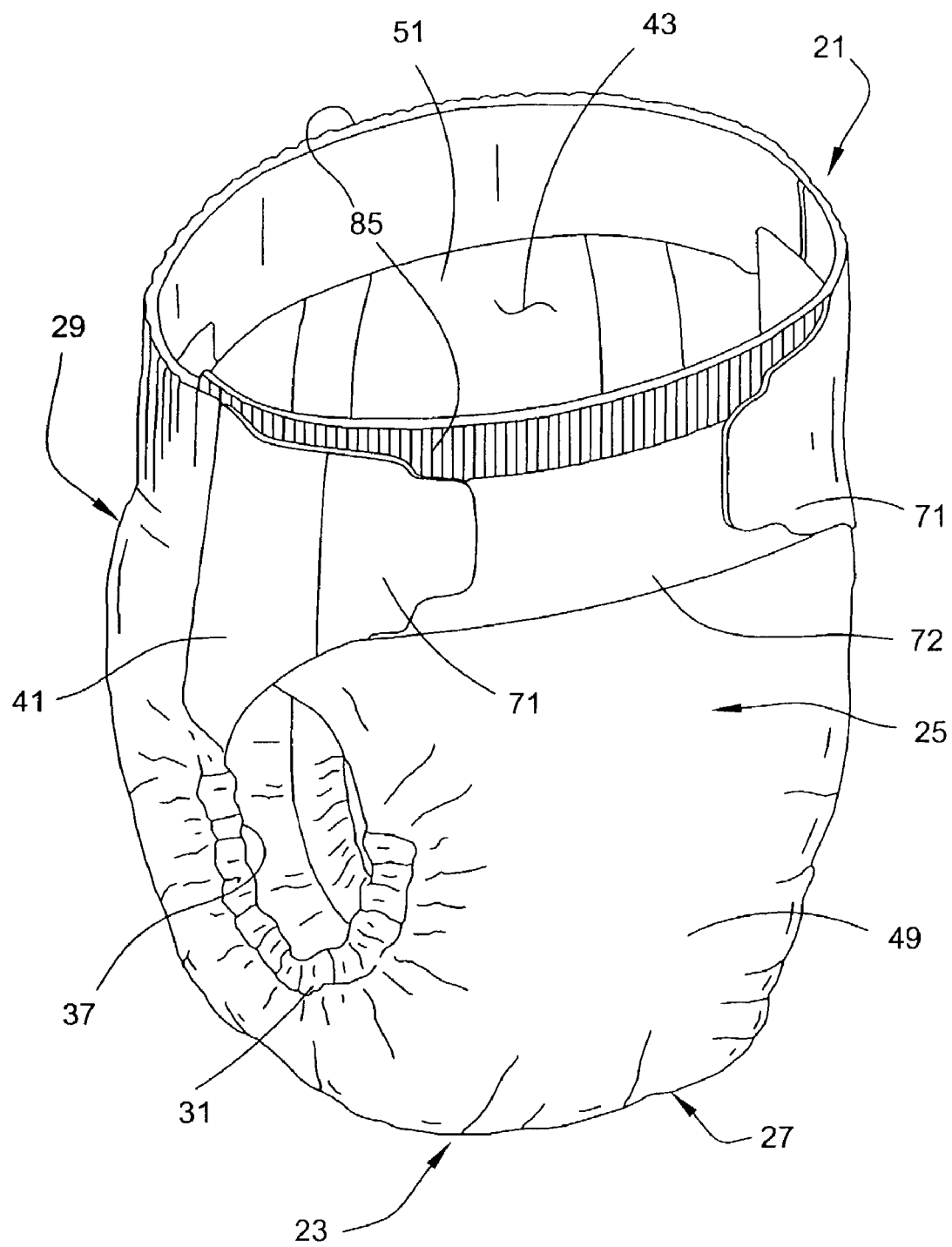
FIG. 3 is a perspective view of the diaper shown as worn.

The diaper 21 is shown in FIG. 1 in an unfolded and laid-flat condition to illustrate a longitudinal axis X and a lateral axis Y of the diaper. The diaper 21 generally comprises a central absorbent assembly 23 extending longitudinally from a front (e.g., anterior) region 25 of the diaper through a crotch (e.g., central) region 27 to a back (e.g., posterior) region 29 of the diaper. The central absorbent assembly 23 is generally I-shaped, and more particularly hourglass shaped, and has contoured, laterally opposite side edges 31 and longitudinally opposite front and rear waist edges or ends, respectively designated 33 and 35. It is understood, however, that the diaper 21 may have other shapes, such as a rectangular shape or a T-shape without departing from the scope of the present invention. The side edges 31 of the diaper 21 extend longitudinally from the front region 25 through the crotch region 27 to the back region 29 for forming transversely spaced leg openings 37 (FIG. 3) of the diaper when worn.

The front region 25 generally includes the portions of the central absorbent assembly 23 which extend over the wearer's lower abdominal region and the back region 29 generally includes the portions of the central absorbent assembly which extend over the wearer's lower back region. The crotch region 27 includes the portion extending longitudinally through the wearer's crotch from the front region 25 to the back region 29 and laterally between the wearer's legs. As worn on the wearer's body (FIG. 3), the diaper 21 further defines a central waist opening 43 and the leg openings 37.

Figure 2:
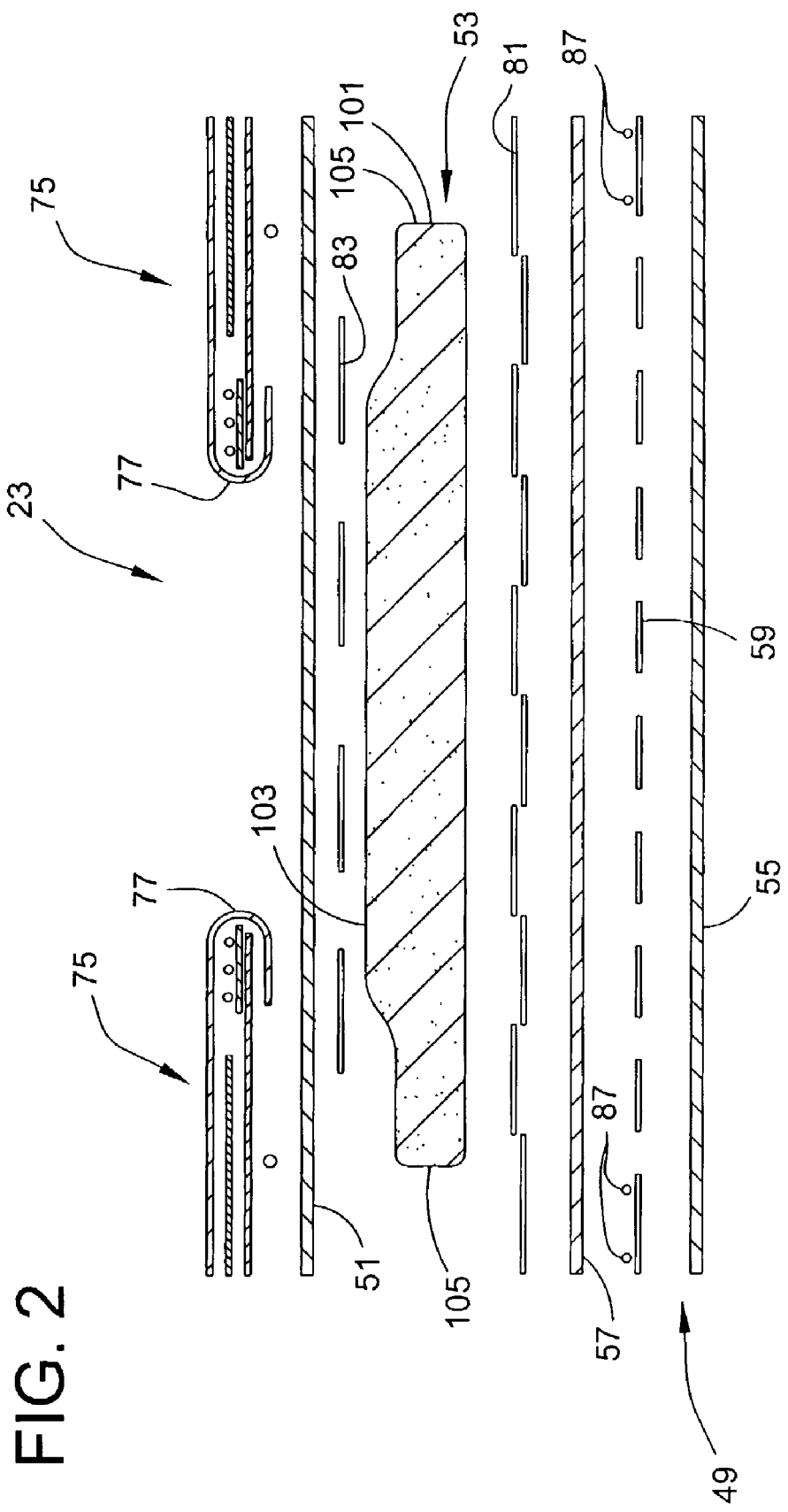
FIG. 2 is an exploded cross section taken generally in the plane including line 2-2 of FIG. 1.

With particular reference to FIG. 2, the central absorbent assembly 23 of the diaper 21 comprises an outer cover, generally indicated at 49, a bodyside liner 51 positioned in facing relation with the outer cover, and an absorbent body, generally indicated at 53, disposed between the outer cover and the liner. The outer cover 49 of the illustrated embodiment generally defines the length and width of the diaper 21. The absorbent body 53 has a length and width which are less than the respective length and width of the outer cover 49 such that the outer cover extends both longitudinally and laterally out beyond the sides and ends of the absorbent body. The bodyside liner 51 may be generally coextensive with the outer cover 49, or may instead overlie an area which is larger (and would thus generally define the length and/or width of the diaper 21) or smaller than the area of the outer cover 49, as desired. In other words, the bodyside liner 51 is preferably in superposed relation with the outer cover 49 but may not necessarily be coextensive with the outer cover.

In one embodiment, the outer cover 49 is stretchable and may or may not be somewhat elastic. More particularly, the outer cover 49 is sufficiently extensible such that once stretched under the weight of the insulted absorbent body, the outer cover will not retract substantially back toward its original position. However, it is contemplated that the outer cover 49 may instead be generally non-extensible and remain within the scope of this invention.

The outer cover 49 may be a multi-layered laminate structure to provide desired levels of extensibility as well as liquid impermeability and vapor permeability. For example, the outer cover 49 of the illustrated embodiment is of two-layer construction, including an outer layer 55 constructed of a vapor permeable material and an inner layer 57 constructed of a liquid impermeable material, with the two layers being secured together by a suitable laminate adhesive 59. It is understood, however, that the outer cover 49 may instead be constructed of a single layer of liquid impermeable material, such as a thin plastic film constructed of materials such as those from which the inner layer 57 is constructed as described later herein, without departing from the scope of this invention. The liquid impermeable inner layer 57 of the outer cover 49 can be either vapor permeable (i.e., "breathable") or vapor impermeable.

The bodyside liner 51 is preferably pliable, soft feeling, and nonirritating to the wearer's skin, and is employed to help isolate the wearer's skin from the absorbent body 53. The liner 51 is less hydrophilic than the absorbent body 53 to present a relatively dry surface to the wearer, and is sufficiently porous to be liquid permeable to thereby permit liquid to readily penetrate through its thickness. A suitable bodyside liner 51 may be manufactured from a wide selection of web materials, but is preferably capable of stretching in at least one direction (e.g., longitudinal or lateral). In particular embodiments, the bodyside liner 51 is desirably extensible and capable of extending along with the outer cover 49 for desired fit of the diaper on the wearer.

Fastener tabs 65 (FIGS. 1 and 3) are secured to the central absorbent assembly 23 generally at the back region 29 thereof with the tabs extending laterally out from the opposite side edges 31 of the assembly. The fastener tabs 65 may be attached to the outer cover 49, to the bodyside liner 51, between the outer cover and liner, or to other components of the diaper 21. The tabs 65 may also be elastic or otherwise rendered elastomeric. For example, the fastener tabs 65 may be an elastomeric material such as a neck-bonded laminate (NBL) or stretch-bonded laminate (SBL) material.

Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference. Alternatively, the fastener tabs 65 may be formed integrally with a selected diaper component. For example, the tabs 65 may be formed integrally with the inner or outer layer 57, 55 of the outer cover 49, or with the bodyside liner 51.

Fastening components, such as hook and loop fasteners, designated 71 and 72 respectively, are employed to secure the diaper 21 on the body of a child or other wearer. Alternatively, other fastening components (not shown), such as buttons, pins, snaps, adhesive tape fasteners, cohesives, mushroom-and-loop fasteners, or the like, may be employed. Desirably, the interconnection of the fastening components 71, 72 is selectively releasable and re-attachable. In the illustrated embodiment, the hook fasteners 71 are secured to and extend laterally out from the respective fastener tabs 65 at the back region 29 of the diaper 21. However, it is understood that the fastener tabs 65 may be formed of a hook material and thus comprise the hook fasteners 71 without departing from the scope of this invention. The loop fastener 72 of the illustrated embodiment is a panel of loop material secured to the outer cover 49 at the front region 25 of the diaper 21 to provide a "fasten anywhere" mechanical fastening system for improved fastening of the hook fasteners 71 with the loop fastener.

The loop material may include a pattern-unbonded nonwoven fabric having continuous bonded areas that define a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded areas that remain sufficiently open or large to receive and engage hook elements of the complementary hook fasteners 71. In particular, a pattern-unbonded non-woven fabric or web may include a spunbond non-woven web formed of single component or multi-component melt-spun filaments. For example, the loop material may be a laminated structure including a polyethylene component and a polypropylene component adhesively bonded together with the polypropylene component facing outward away from the outer cover 49 to receive the hook fasteners 71. Examples of suitable pattern-unbonded fabrics are described in U.S. Pat. No. 5,858,515 issued Jan. 12, 1999 to T. J. Stokes et al. and entitled PATTERN-UNBONDED NON-WOVEN WEB AND PROCESS FOR MAKING THE SAME; the entire disclosure of which is incorporated herein by reference in a manner that is consistent herewith.

The diaper 21 shown in FIG. 1 also comprises a pair of containment flaps, generally indicated at 75, configured to provide a barrier to the lateral flow of body exudates. The containment flaps 75 are located generally adjacent the laterally opposite side edges 31 of the diaper 21 and, when the diaper is laid flat as shown in FIGS. 1 and 2, extend inward toward the longitudinal axis X of the diaper. Each containment flap 75 typically has a free, or unattached end 77 free from connection with the bodyside liner 51 and other components of the diaper 21. Elastic strands 79 disposed within the flaps 75 adjacent the unattached ends thereof urge the flaps toward an upright, perpendicular configuration in at least the crotch region 27 of the diaper 21 to form a seal against the wearer's body when the diaper is worn. The containment flaps 75 may extend longitudinally the entire length of the absorbent body 53 or they may extend only partially along the length of the absorbent body. When the containment flaps 75 are shorter in length than the absorbent body 53, the flaps can be selectively positioned anywhere between the side edges 31 of the diaper 21 in the crotch region 27. In a particular aspect of the invention, the containment flaps 75 extend the entire length of the absorbent body 53 to better contain the body exudates.

Such containment flaps 75 are generally well known to those skilled in the art and therefore will not be further described herein except to the extent necessary to describe the present invention. As an example, suitable constructions and arrangements for containment flaps 75 are described in U.S. Pat. No. 4,704,116 issued Nov. 3, 1987, to K. Enloe, the disclosure of which is hereby incorporated by reference. The diaper 21 may also incorporate other containment components in addition to or instead of the containment flaps 75. For example, while not shown in the drawings, other suitable containment components may include, but are not limited to, elasticized waist flaps, foam dams in the front, back and/or crotch regions, and the like.

The various components of the diaper 21 are assembled together using a suitable form of attachment, such as adhesive, sonic bonds, thermal bonds or combinations thereof. In the illustrated embodiment, the outer cover 49 and absorbent body 53 are secured to each other with lines of adhesive 81, such as a hot melt or pressure-sensitive adhesive. The bodyside liner 51 is also secured to the outer cover 49 and may also be secured to the absorbent body 53 using the same forms of attachment.

The bodyside liner 51 may be secured to the outer cover 49 at the lateral edge margins of the crotch region 27, but at least the central portion is free of such connection. Rather than being entirely free of such connection, the bodyside liner 51 may be secured to the absorbent body 53 in the crotch region 27 by a light adhesive 83 which will break away in use. Preferably, securement of the bodyside liner 51 to the outer cover 49 is limited to overlying peripheral edge margins of the two to promote independent stretching movement of the liner and cover relative to each other. If the diaper 21 is to be sold in a pre-fastened condition, the diaper may also have passive bonds (not shown) which join the back region 29 with the front region 25.

The diaper 21 can also include a surge management layer (not shown) which helps to decelerate and diffuse surges or gushes of liquid that may be rapidly introduced into the absorbent body 53. Desirably, the surge management layer can rapidly accept and temporarily hold the liquid prior to releasing the liquid to the absorbent structure. In the illustrated embodiment, for example, a surge layer can be located between the absorbent body 53 and the bodyside liner 51. Examples of suitable surge management layers are described in U.S. Pat. No. 5,486,166 entitled FIBROUS NON-WOVEN WEB SURGE LAYER FOR PERSONAL CARE ABSORBENT ARTICLES AND THE LIKE by C. Ellis and D. Bishop, which issued Jan. 23, 1996, and U.S. Pat. No. 5,490,846 entitled IMPROVED SURGE MANAGEMENT FIBROUS NON-WOVEN WEB FOR PERSONAL CARE ABSORBENT ARTICLES AND THE LIKE by C. Ellis and R. Everett, which issued Feb. 13, 1996, the entire disclosures of which are hereby incorporated by reference in a manner that is consistent herewith.

To provide improved fit and to help further reduce leakage of body exudates from the diaper 21, elastic components are typically incorporated therein, particularly at the waist area and the leg areas. For example, the diaper 21 of the illustrated embodiment has waist elastic components 85 (FIG. 3) and leg elastics 87 (FIGS. 1 and 2). The waist elastic components 85 are configured to gather and shirr the end margins of the diaper 21 to provide a resilient, comfortable close fit around the waist of the wearer and the leg elastics 87 are configured to gather and shirr the side margins of the diaper at the leg openings 37 to provide a close fit around the wearer's legs.

Examples of other diaper 21 configurations suitable for use in connection with the instant application that may or may not include diaper components similar to those described previously are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., U.S. Pat. No. 5,509,915 issued Apr. 23, 1996 to Hanson et al., U.S. Pat. No. 5,993,433 issued Nov. 30, 199 to St. Louis et al., and U.S. Pat. No. 6,248,097 issued Jun. 19, 2001 to Beitz et al., the disclosures of which are herein incorporated by reference.

Figure 4:
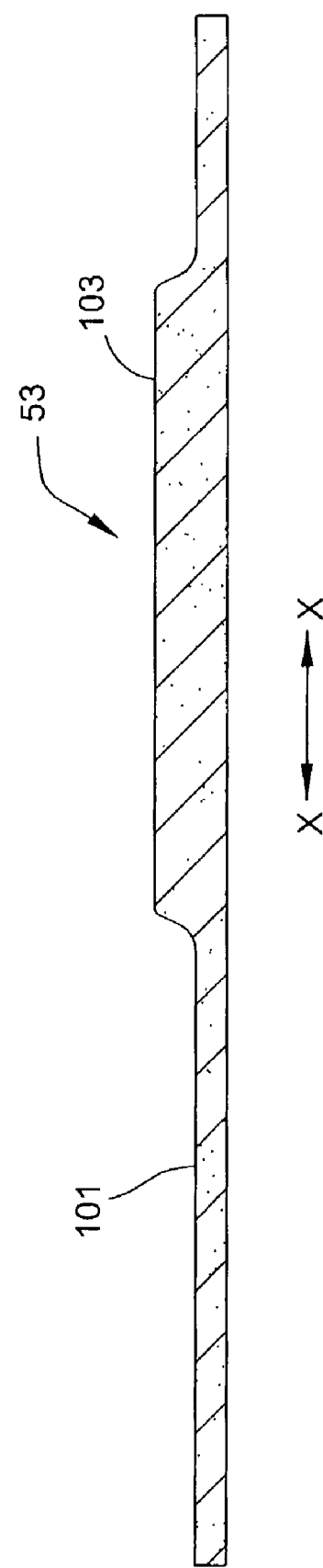
FIG. 4 is a longitudinal cross-section of an absorbent structure of the diaper of FIG. 1 taken generally on the longitudinal axis thereof.

In accordance with the present invention, the absorbent body 53 at least in part comprises a stabilized non-woven absorbent structure 101 (FIG. 4) formed from a mixture of absorbent fibers, superabsorbent material (the absorbent fibers and superabsorbent material together broadly defining an absorbent material within the absorbent structure) and binder fibers (broadly, a binding material) which are activatable as will be described to form inter-fiber bonds within the absorbent structure for stabilizing the absorbent structure.

The absorbent fibers may be provided by various types of wettable, hydrophilic fibrous material. For example, suitable absorbent fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. For the present invention, it is contemplated that selected blends of the various types of fibers mentioned above may also be employed.

Suitable sources of absorbent fibers may include cellulosic fibers including: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. High-yield fibers, such as BCTMP (Bleached ChemiThermal Mechanical Pulp) fibers, can be flash-dried and compressed into densified pads. The high-yield fiber can expand to a higher loft when wetted, and can be used for the absorbent fiber material. Other absorbent fibers, such as regenerated cellulose and curled chemically stiffened cellulose fibers may also be densified to form absorbent structures that can expand to a higher loft when wetted.

As an example, suitable wood pulps include standard softwood fluffing grade such as NB-416 (Weyerhaeuser Corporation, Tacoma, Wash., U.S.A.) and CR-1654 (US Alliance Pulp Mills, Coosa, Ala., U.S.A.), bleached kraft softwood or hardwood, high-yield wood fibers, ChemiThermoMechanical Pulp fibers and Bleached Chemithermal Mechanical Pulped (BCTMP). Pulp may be modified in order to enhance the inherent characteristics of the fibers and their processability. Curl may be imparted to the fibers by conventional methods including chemical treatment or mechanical twisting. Pulps may also be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns.

Pulp may also be stiffened by the use of heat or caustic treatments such as mercerization. Examples of these types of fibers include NHB416 which is a chemically crosslinked southern softwood pulp which enhances wet modulus, available from the Weyerhaeuser Corporation of Tacoma, Wash., U.S.A. Other useful pulps are debonded pulp (NF405) also from Weyerhaeuser. HPZ3 from Buckeye Technologies, Inc of Memphis, Tenn., U.S.A., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incorporated of Axis, Ala., U.S.A.

Superabsorbent materials useful in forming the absorbent structure 101 may be chosen based on chemical structure as well as physical form. These include superabsorbent materials with low gel strength, high gel strength, surface cross-linked superabsorbent materials, uniformly cross-linked superabsorbent materials, or superabsorbent materials with varied cross-link density throughout the structure 101. The superabsorbent materials may be based on chemistries that include poly(acrylic acid), poly(iso-butylene-co-maleic anhydride), poly(ethylene oxide), carboxy-methyl cellulose, poly(-vinyl pyrrollidone), and poly(-vinyl alcohol). The superabsorbent materials may range in swelling rate from slow to fast.

The superabsorbent materials of the absorbent structure 101 of the present invention are desirably particulate. However, the superabsorbent materials may alternatively be in the form of foams, macroporous or microporous particles or fibers, particles or fibers with fibrous or particulate coatings or morphology. The superabsorbent materials may be in various length and diameter sizes and distributions and may also be in various degrees of neutralization. Counter-ions are typically Li, Na, K, Ca.

An exemplary superabsorbent material is available from Stockhausen, Inc of Greensboro, N.C., U.S.A. and is designated FAVOR® SXM 880. Another exemplary superabsorbent material may be obtained from the Dow Chemical Company of Midland, Mich., U.S.A. under the name DRYTECH® 2035. A suitable fibrous superabsorbent material is available from Camelot Technologies, Ltd., of River, Alberta, Canada and is designated FIBERDRI® 1241. Another suitable superabsorbent material is available from Chemtall Inc. of Riceboro, Ga., and is designated FLOSORB 60 LADY®, also known as LADYSORB 60®.

The binder fibers are desirably activatable, such as upon being heated, to form inter-fiber bonds within the absorbent structure. As used herein, the inter-fiber bonds may be between the binder fibers and the absorbent fibers, between the binder fibers and the superabsorbent material, and/or among the binder fibers themselves.

In one embodiment, the binder fibers are bicomponent, or multicomponent binder fibers. As used herein, multicomponent fibers refers to fibers formed from two (e.g., bicomponent) or more polymers extruded from separate extruders but joined together to form a single fiber. The polymers are arranged in substantially constantly positioned distinct zones across a cross-section of the multi-component fibers and extend continuously along at least a portion of, and more desirably the entire, length of the fiber. The configuration of the multi-component fibers may be, for example, a sheath/core arrangement in which one polymer is surrounded by another, a side-by-side arrangement, a pie arrangement, an "islands-in-the-sea" arrangement or other suitable arrangement. Bicomponent fibers are disclosed in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Bicomponent fibers are also taught in U.S. Pat. No. 5,382,400 to Pike et al. and may be used to produce crimp in the fibers by using the differential rates of expansion and contraction of the two (or more) polymers.

Multicomponent binder fibers as used herein refers to multicomponent fibers in which at least one of the binder fiber components has a melt temperature that is less than at least one other binder fiber component. For example, the binder fiber may be a bicomponent fiber having a sheath/core arrangement in which the sheath component of the binder has a melt temperature that is lower than the melt temperature of the core component of the binder fiber. Upon heating of the binder fiber, the component having the lower melt temperature can fuse and bond to nearby absorbent fibers, superabsorbent material or other binder fibers while the other component, or components, remain in a generally unmelted state so as to generally maintain the integrity of the binder fiber.

In other embodiments, the binder fibers can be monofilament or homofilament fibers, biconstituent fibers and the like, as well as combinations thereof.

The binder fibers are desirably constructed of a material, or material, that are readily heated upon exposure to an activation energy, and more particularly the binder fibers are desirably susceptible to dielectric heating via exposure to electromagnetic energy wherein the binder fibers are melted to facilitate forming inter-fiber bonds within the absorbent structure.

Dielectric heating is the term applied to the generation of heat in non-conducting materials by their losses when subject to an alternating electric field of high frequency. For example, the frequency of the electric field desirably ranges from about 0.01 to about 300 GHz (billion cycles/sec). Heating of non-conductors by this method is extremely rapid. This form of heating is applied by placing the non-conducting material between two electrodes, across which the high-frequency voltage is applied. This arrangement in effect constitutes an electric capacitor, with the load acting as the dielectric. Although ideally a capacitor has no losses, practical losses do occur, and sufficient heat is generated at high frequencies to make this a practical form of heat source.

The frequency used in dielectric heating is a function of the power desired and the size of the object being heated. Practical values of voltages applied to the electrodes are 2000 to 5000 volts/in of thickness of the object. The source of power is by electronic oscillators that are capable of generating the very high frequencies desirable.

The basic requirement for dielectric heating is the establishment of a high-frequency alternating electric field within the material or object to be heated. Once the electric field has been established, the second requirement involves dielectric loss properties of the material to be heated. The dielectric loss of a given material occurs as a result of electrical polarization effects in the material itself and may be through dipolar molecular rotation and ionic conduction. The higher the dielectric loss of a material, the more receptive to the high frequency energy it is.

In one embodiment, the electromagnetic energy is radio frequency or RF radiation, which occurs at about 27 MHz and heats by providing some portion of the total power delivered as ionic conduction to the molecules within the workpiece, with much of the remainder of the power delivered as dipolar molecular rotation.

In another embodiment, the electromagnetic energy is microwave radiation, which is dielectric heating at still higher frequencies. The predominate frequencies used in microwave heating are 915 and 2450 MHz. Microwave heating is 10 to 100 times higher in frequency than the usual dielectric heating, resulting in a lower voltage requirement if the loss factor is constant, though the loss factor is generally higher at microwave frequencies.

Microwave radiation can penetrate dielectric materials and be absorbed uniformly, thereby generating heat uniformly. Microwave energy is also selectively absorbed, offering a means for self-limiting the energy taken up by heterogeneous materials, making overheating less likely. These combined effects allow microwave heating to be more rapid, with less heating of surrounding materials, with a low thermal lag, and therefore with good control.

It is understood that the binder fibers or other suitable binding material may be activatable other than by dielectric heating, such as by convective or infrared heating or other non-thermal activation, as long as the binder fibers can be incorporated into the absorbent structure 101 prior to activation of the binder fibers to form inter-fiber bonds within the absorbent structure and then subsequently activated to form such inter-fiber bonds to thereby form the stabilized absorbent structure 101.

The binder fibers desirably have a fiber length which is at least about 0.061 mm. The binder fiber length can alternatively be at least about 3 mm and can optionally be at least about 6 mm. In a further feature, the binder-fibers can have a length of up to about 30 mm or more. The binder fiber length can alternatively be up to about 25 mm, and can optionally be up to about 19 mm. In a further aspect, the absorbent structure 101 may include binder fibers having lengths approximating one of the dimensions (e.g., length or width) of the absorbent structure. A relatively long binder fiber length provides an increased number of inter-fiber bond points upon activation of the fibers to help generate improved integrity and permeability of the absorbent structure 101.

Synthetic fibers suitable for use as binder fibers in the absorbent structure 101 include those made from synthetic matrix polymers like polyolefins, polyamides, polycaprolactones, polyetheramides, polyurethanes, polyesters, poly(meth) acrylates metal salts, polyether, poly(ethylene-vinyl acetate) random and block copolymers, polyethylene-b-polyethylene glycol block copolymers, polypropylene oxide-b-polyethylene oxide copolymers (and blends thereof) and any other suitable synthetic fibers known to those skilled in the art.

In one embodiment, an energy receptive additive can be included in the binder fibers during production thereof wherein the additive allows the binder fibers to reach their melting temperature much more rapidly than without the additive. This allows inter-fiber bonding in the absorbent structure 101 to occur at a faster rate than without the additive. The additive is desirably capable of absorbing energy at the frequency of electromagnetic energy (e.g., between 0.01 GHz and 300 GHz) rapidly, such as in the range of fractions of a second, desirably less than a quarter of a second and at most about half a second. However, it is contemplated that absorbent structures which involve the absorption of energy and bonding of the binder fibers with the absorbent fibers over a period as long as about 30 seconds are intended to be within the scope of this invention. Melting of the binder fibers will depend on a number of factors such as generator power, additive receptivity, fiber denier, which is generally between 1 and 20, and the composition of the matrix polymer of the binder fiber.

The energy receptive additive may be added to a fiber-making matrix polymer as it is compounded, or coated onto the binder fiber after the fiber is produced. A typical method of compounding the additive with the matrix polymer is with a twin screw extruder, which thoroughly mixes the components prior to extruding them. Upon extrusion, the polymer blend is usually pelletized for convenient storage and transportation.

If the binder fiber is a bicomponent fiber, the energy receptive additive may be added to either or both of the fiber components. The energy receptive additive may also be added to one or more components, preferably the continuous phase, of a biconstituent fiber, and intermittently distributed throughout the length and cross-section of the fiber. If the additive to be used is not compatible with the matrix polymer into which it is to be blended, a "compatibilizer" may be added to enhance the blending. Such compatibilizers are known in the art and examples may be found in U.S. Pat. Nos. 5,108,827 and 5,294,482 to Gessner.

The energy receptive additives can be receptive to various specific spectra of energy. Just as a black item will absorb more energy and become warmer than the same item colored white when subjected to the same amount of solar energy, energy receptive additives will absorb energy at their specific wavelength, directed at them.

A successful energy receptive additive should have a dielectric loss factor, as discussed previously, which is relatively high. The energy receptive additives useful in this invention typically can have a dielectric loss factor measured in the RF or microwave frequency of between about 0.5 and 15, more particularly between about 1 and 15, and still more particularly between about 5 and 15. It should be noted that the dielectric loss factor is a dimensionless number. It is preferred that the fiber have a dielectric loss tangent of between about 0.1 and about 1, and more particularly between about 0.3 and about 0.7.

The energy receptive additive may be, for example, carbon black, magnetite, silicon carbide, calcium chloride, zircon, alumina, magnesium oxide, and titanium dioxide. The energy receptive additive may be present in an amount between 2 and 40 weight percent, and more particularly between 5 and 15 weight percent. The binder fibers may be crimped, extendible and/or elastic.

Synthetic fibers incorporating such energy receptive additives are discussed at greater length in co-assigned U.S. patent application Ser. No. 10/034,079 filed Dec. 20, 2001 and entitled Targeted Bonding Fibers for Stabilized Absorbent Structures, the entire disclosure of which is incorporated herein by reference. Absorbent structures incorporating binder fibers having such energy receptive additives are discussed in co-assigned U.S. patent application Ser. No. 10/033,860 filed Dec. 20, 2001 and entitled Targeted On-Line Stabilized Absorbent Structures.

In addition to the binder fibers having an energy receptive additive, or as an alternative thereto, the binder fibers (or at least one binder fiber component thereof where the binder fiber is a multicomponent fiber) may be constructed to have a relatively low melting temperature, such as less than about 200° C., more desirably less than about 150° C., even more desirably less than about 110° C., still more desirably less than about 90° C., and most desirably less than about 80° C. In such an instance, the absorbent fibers and superabsorbent material of the absorbent structure 101 can act as a source of heat to indirectly transfer energy to melt the low melting temperature binder fibers. The absorbent fibers thus act as an energy receptive material, and are excited to melt the adjacent low melting temperature polymers of the binder fibers for bonding to the absorbent fibers, to the superabsorbent material and/or to each other. This melting will depend on a number of factors such as generator power, moisture content, specific heat, density of the absorbent structure 101 materials, fiber denier, which is generally between 1 and 20, and the composition and concentration of the low melting temperature polymers of the binder fibers.

The low melting temperature binder fibers desirably have a low specific heat to allow rapid heating and cooling of the absorbent structure 101. The low specific heat is useful during the heating cycle since the heat absorbed by the binder fiber before melting is relatively low. The low specific heat is also useful during subsequent cooling of the absorbent structure 101, since the heat to be removed from the binder fiber material to cause it to solidify and stabilize the absorbent structure will be lower. A suitable specific heat range of the binder fiber is in the range of about 0.1 to about 0.6 calories/gram.

The binder fibers also desirably have a high thermal conductivity to enable rapid transfer of heat therethrough. Thermal conductivity is proportional to density and heat capacity/specific heat capacity of the binder fiber material. It is beneficial to achieve higher thermal conductivity using fibers with relatively high density. For example, the binder fibers desirably have a density of more than about 0.94 grams/cubic centimeter (g/cc). This is helpful in accelerating the heating and cooling cycles during activation of the binder fibers to stabilize the absorbent structure 101. It is preferred that the thermal conductivity of the binder fibers be greater than about 0.1 joules-sec$^{-1}$-mole$^{-1}$-degree Kelvin$^{-1}$.

Materials having a low melting enthalpy are also desirable for use as the binder fibers. The low melting enthalpy reduces the energy requirement for transformation of the binder fiber from a solid to a molten state during heating thereof and from the molten state back to a solid state during subsequent cooling. As an example, the melting enthalpy of the binder fibers is desirably less than about 100 joules/gram, more particularly less than about 75 joules/gm and still more particularly less than about 60 joules/gm.

The binder fibers also desirably have a low melt viscosity after activation, i.e., once the fiber is transformed from its solid to its generally molten state. This enables the binder fiber material to flow to the junction points between the binder fibers and the absorbent fibers, superabsorbent material and/or other binder fibers for forming stable inter-fiber bonds. As an example, it is desired that the melt viscosity of the binder fibers be less than about 100,000 centipoise, more particularly less than about 20,000 centipoise and most particularly less than about 10,000 centipoise.

The binder fibers also desirably have adequate surface energy to be wettable by fluid to be absorbed by the absorbent structure 101. This wettability is not required in all applications, however, and may be accomplished using various surfactants known to those skilled in the art if the binder fiber is not intrinsically wettable.

Suitable binder fibers having a low melting temperature may be made from polyethylene-polyvinyl alcohol (PE-PVA) block or random copolymers, polyethylene-polyethylene oxide (PE-PEO) block/graft copolymers, polypropylene-polyethylene oxide (PP-PEO) block/graft copolymers, polyester, polycaprolactone, polyamide, polyacrylates, polyurethane (ester or ether based). The melting point can be adjusted by adjusting the content of VA or PEO (for those polymers with VA and PEO) or the configuration. The binder fiber material can be made by compounding with a twin extruder, Sigma mixer or other compounding equipment and then made into fibers by conventional non-woven processes like meltblowing and spunbonding.

As an example, absorbent structures incorporating such low melting temperature binder fibers are discussed in co-assigned U.S. application Ser. No. 10/034,021, filed Dec. 20, 2002 and entitled Absorbent Structures Having Low Melting Fibers, the entire disclosure of which is incorporated herein by reference.

A number of other polymers and sensitizers may also, or may alternatively, be used with the energy receptive additives in making the binder fibers. Specifically selecting and/or positioning moieties along the polymer chain can affect the dielectric loss factor of the polymer and enhance the responsiveness of the polymer to electromagnetic energy. These include polymer composites from blend, block, graft, random copolymers, ionic polymers and copolymers and metal salts. Desirably, the presence of one or more moieties along the polymer chain causes one or more of the following: (1) an increase in the dipole moments of the polymer; and (2) an increase in the unbalanced charges of the polymer molecular structure. Suitable moieties include, but are not limited to, aldehyde, ester, carboxylic acid, sulfonamide and thiocyanate groups.

The selected moieties may be covalently bonded or ionically attached to the polymer chain. As discussed above, moieties containing functional groups having high dipole moments are desired along the polymer chain. Suitable moieties include, but are not limited to, urea, sulfone, amide, nitro, nitrile, isocyanate, alcohol, glycol and ketone groups. Other suitable moieties include moieties containing ionic groups including, but are not limited to, sodium, zinc, and potassium ions.

For example, a nitro group may be attached to an aryl group within the polymer chain. It should be noted that the nitro group may be attached at the meta or para position of the aryl group. Further, it should be noted that other groups may be attached at the meta or para position of the aryl group in place of the nitro group. Suitable groups include, but are not limited to, nitrile groups. In addition to these modifications, one could incorporate other monomer units into the polymer to further enhance the responsiveness of the resulting polymer. For example, monomer units containing urea and/or amide groups may be incorporated into the polymer.

Suitable moieties include aldehyde, ester, carboxylic acid, sulfonamide and thiocyanate groups. However, other groups having or enhancing unbalanced charges in a molecular structure can also be useful; or a moiety having an ionic or conductive group such as, e.g., sodium, zinc, and potassium ions. Other ionic or conductive groups may also be used.

Specific combinations include low density PE/polyethylene-polyvinylacetate block copolymer, LDPE/polyethylene glycol, PE/polyacrylates, polyethylene-vinyl acetate copolymer, polyester, polyurethane, polyacrylates, polyethylene glycol (PEG), polyacrylamide (PAA), polyethylenimine (PEEM), polyvinyl acetate (PVAC), polyvinyl alcohol (PVA), polymethylacylic acid-sodium salt (PMA-Na), polyacylic acid sodium salt (PA-Na), and poly (styrene solfonate-co-methyl acylic acid) sodium salt (P (SS-co-MA)-Na), and polymers of terephthalic acid, adipic acid and 1,4 butanediol, and polybutylene succinate copolymers. Other materials include polymers of terephtalic acid, adipic acid and 1,4-butanediol, sold by BASF Corporation under the name ECOFLEX® or by Eastman Chemical Co. under the name Eastar Bio™ copolyester. Blends and grafted copolymers of the above listed polymers are also suitable.

The absorbent structure 101 of the present invention is desirably of unitary construction. As used herein, the unitary construction of the absorbent structure 101 means that the absorbent structure is a single non-woven web or layer comprising a mixture of absorbent fibers, binder fibers and, optionally, superabsorbent material. In the illustrated embodiment of FIGS. 1-4, a single absorbent structure 101 comprises substantially the entire absorbent body 53 of the diaper 21 (i.e., the dimensions of the absorbent structure substantially define the dimensions of the absorbent body). However, it is contemplated that the absorbent body 53 may comprise more than one layer, wherein at least one of the layers is an absorbent structure 101 of the present invention, and remain within the scope of this invention as long as the absorbent structure is itself of unitary construction.

As an example, in one embodiment the absorbent structure 101 is made by first forming or otherwise collecting the absorbent fibers, superabsorbent material and binder fibers into a unitary structure having a desired shape, contour and/or material distribution prior to activation of the binder fibers (e.g., prior to inter-fiber bonding within the absorbent structure) to define a non-woven, generally pre-stabilized absorbent structure. The binder fibers are subsequently activated to form inter-fiber bonds within absorbent structure to thereby stabilize the absorbent structure.

Optionally, a substantially hydrophilic tissue wrapsheet (not illustrated) may be employed to help maintain the integrity of the absorbent structure 101, or the entire absorbent body 53. The tissue wrapsheet is typically placed about the absorbent structure or the absorbent body over at least the two major facing surfaces thereof and is composed of an absorbent cellulosic material, such as creped wadding or a high wet-strength tissue. The tissue wrapsheet can also be configured to provide a wicking layer that helps to rapidly distribute liquid to the absorbent fibers within the absorbent body 53. The wrapsheet material on one side of the absorbent body may be bonded to the wrapsheet located on the opposite side of the fibrous mass to effectively entrap the absorbent body.

In one embodiment, the material composition of the pre-stabilized absorbent structure 101 (e.g., prior to activation of the binder fibers) may be from about 0.1 to about 60 weight percent binder fiber, from about 0 to about 80 weight percent superabsorbent material, and from about 5 to about 98 weight percent absorbent fibers. More particular embodiments may have from about 2 to about 10 weight percent binder fiber, from about 30 to about 70 weight percent superabsorbent material and from about 30 to about 70 weight percent absorbent fiber. In other embodiments, the pre-stabilized absorbent structure may have from about 0.1 to about 5 weight percent binder fiber.

In another embodiment, the pre-stabilized absorbent structure 101 can include an amount of binder fibers which is at least about 0.1 weight percent with respect to the total weight of the absorbent structure. The amount of binder fibers can alternatively be at least about 1 weight percent, and can optionally be at least about 3 weight percent. In other aspects, the amount of binder fibers can be up to a maximum of about 30 weight percent, or more. The amount of binder fibers can alternatively be up to about 20 weight percent, and can optionally be up to about 5 weight percent.

The absorbent fibers, binder fibers and superabsorbent material are desirably distributed within the absorbent structure generally across the full width of the absorbent structure, along the full length thereof and throughout the thickness thereof. However, the concentration of absorbent fibers, binder fibers and/or superabsorbent material within the absorbent structure 101 may be non-uniform i) across the width of the absorbent structure, ii) along the length of the absorbent structure, and/or iii) along the thickness or z-direction 127 of the absorbent structure. For example, a heavier concentration of absorbent fibers, binder fibers and/or superabsorbent material may be disposed in different strata (e.g., in the z-direction) or in different regions (e.g., along the length or across the width) of the absorbent structure.

It is also contemplated that one or more strata or regions of the absorbent structure 101 may be devoid of binder fibers and/or superabsorbent material, as long as the absorbent structure is of unitary construction and includes binder fibers in at least a portion of the structure. It is further contemplated that binder fibers constructed of different materials may be disposed in different strata or regions of the absorbent structure 101 without departing from the scope of this invention.

The average basis weight of the pre-stabilized absorbent structure 101 is desirably in the range of about 30 to about 2500 grams/square meter (gsm), more desirably within the range of about 50 to about 2000 gsm, and even more desirably within the range of about 100 to about 1500 gsm. The pre-stabilized absorbent structure 101 can also be formed to have a non-uniform basis weight across its width or along its length, with one or more high basis weight regions, and one or more low basis weight regions. In at least one high basis weight region, at least a significant portion of the absorbent structure 101 can have a composite basis weight which is at least about 700 gsm. The high basis weight region can alternatively have a basis weight of at least about 750 gsm, and can optionally have a basis weight of at least about 800 gsm. In other aspects, the high basis weight region of the absorbent structure 101 can have a composite basis weight of up to about 2500 gsm or more. The high basis weight region can alternatively have a basis weight of less than or equal to about 2000 gsm, and more particularly less than or equal to about 1500 gsm.

Additionally, in at least one low basis weight region, the pre-stabilized absorbent structure 101 can have a composite basis weight of at least about 50 gsm. The low basis weight region can alternatively have a basis weight of at least about 100 gsm, and can optionally have a basis weight of at least about 150 gsm. In another alternative configuration, the low basis weight region of the absorbent structure 101 can have a composite basis weight of up to about 700 gsm, or more. The low basis weight region can alternatively have a basis weight of up to about 600 gsm, and can optionally have a basis weight of up to about 500 gsm.

In another aspect of the present invention, the absorbent structure 101 formed prior to activation of the binder fibers may have a density which is at least a minimum of about 0.01 g/cc as determined at a restraining pressure of 1.38 KPa (0.2 psi). The density can alternatively be at least about 0.02 g/cc, and can optionally be at least about 0.03 g/cc. In other aspects, the density may be up to a maximum of about 0.12 g/cc, or more. The density can alternatively be up to about 0.11 g/cc, and can optionally be up to about 0.1 g/cc. In one embodiment, the density of the pre-stabilized absorbent structure is substantially uniform throughout the absorbent structure. In another embodiment, the density is non-uniform across the width of the absorbent structure and/or along the length of the absorbent structure.

As used throughout the present application, the term "non-uniform" as used in reference to a particular characteristic or feature of the absorbent structure, is intended to mean that the characteristic or feature is non-constant or otherwise varies within the absorbent structure in accordance with a pre-determined non-uniformity, e.g., an intended non-uniformity that is greater than non-uniformities resulting from normal processing and tolerance variations inherent in making absorbent structures. The non-uniformity may be present as a either a gradual gradient or as a stepped gradient, such as where the concentration, basis weight and/or density changes abruptly from one strata or region to an adjacent strata or region within the absorbent structure, and may occur repeatedly within the absorbent structure or may be limited to a particular portion of the absorbent structure.

The pre-stabilized absorbent structure 101 may also be formed to have a thickness which is non-uniform along the length of the absorbent structure and/or across the width of the absorbent structure. The thickness is the distance between the major faces the absorbent structure, as determined in a local z-direction of the absorbent structure directed perpendicular to the planes of the major faces thereof at the location at which the thickness is determined. A variation in thickness may be present as a gradual or otherwise sloped change in thickness or as a stepped change in thickness whereby the thickness changes abruptly from one portion of the absorbent structure to an adjacent portion.

Accordingly, one or more portions of the absorbent structure 101 can have a relatively lower thickness, and other portions of the absorbent structure can have a relatively higher thickness. For example, in the illustrated embodiment, a portion 103 (FIGS. 2 and 4) of the absorbent structure 101 which forms the absorbent body 53 of the diaper 21 is substantially thicker than the rest of the absorbent structure and corresponds generally to the front region 25 of the diaper to provide a targeted area of increased absorption capacity. The thicker portion 103 of the absorbent structure 101 extends lengthwise less than the full length of the absorbent structure and is spaced longitudinally inward of the longitudinal ends of the structure. As shown in FIG. 2 the thicker portion 103 is also centrally positioned between the side edges 105 of the absorbent structure and spaced laterally inward from the side edges thereof.

Additionally, or alternatively, the pre-stabilized absorbent structure 101 may be formed to have a non-uniform width along the length of the absorbent structure. The width is the distance between the side edges of the absorbent structure, as determined in a direction parallel to the Y-axis of the absorbent structure. A variation in width may be present as a gradual or otherwise sloped change in width or as a stepped change in width in which the width changes abruptly from one portion of the absorbent structure to an adjacent portion. As an example, the absorbent structure 101 may have any of a number of shapes, including rectangular, I-shaped, or T-shaped and is desirably narrower in the crotch region 27 than in the front or back regions 25, 29 of the diaper 21. As illustrated in phantom in FIG. 1, the shape of the absorbent body 53 is defined by the absorbent structure 101 and is generally T-shaped, with the laterally extending crossbar of the "T" generally corresponding to the front region 25 of the diaper 21 for improved performance, especially for male infants.

It is understood, however, that the pre-stabilized absorbent structure 101 may have a substantially uniform thickness and/or may have a substantially uniform width, i.e., the side edges 105 of the absorbent structure are substantially straight and in generally parallel relationship with each other along the length of the absorbent structure.

The absorbent structure 101 is formed in accordance with a desired method for making such an absorbent structure whereby the absorbent fibers, superabsorbent material and binder fibers are collected on a forming surface while the binder fibers are in a pre-activated condition. The absorbent structure 101 is thus formed as a unitary structure having a desired shape and contour (e.g., a desired length, width and/or thickness profile) before activation of the binder fibers occurs, i.e., before inter-fiber bonding occurs within the absorbent structure. The distribution of fibers and superabsorbent material within the pre-stabilized absorbent structure 101 may also be controlled during formation thereof so that the concentration of materials, basis weight and/or density is substantially non-uniform prior to activation of the binder fibers. The orientation of the absorbent fibers and binder fibers within the absorbent structure is desirably generally random following formation of the pre-stabilized absorbent structure, including at the major faces, side edges and longitudinal ends of the absorbent structure.

The binder fibers are then activated to form inter-fiber bonds with the absorbent fibers, the superabsorbent material and/or other binder fibers to stabilize the absorbent structure 101. More particularly, in one embodiment the pre-stabilized absorbent structure 101 is exposed to high-frequency electromagnetic energy (e.g., microwave radiation, radio frequency radiation, etc.) to melt the binder fibers for inter-fiber bonding with the absorbent fibers, and then cooled to generally solidify the binder fibers to thereby secure the inter-fiber bonds between the binder fibers and the absorbent fibers.

The absorbent structure desirably remains unmolded during and after activation of the binder fibers. As used herein, the term unmolded during and after activation of the binder fibers means that the binder fibers are not subjected to an operation in which the shape and/or orientation thereof within the absorbent structure, and particularly at the major faces, side edges and longitudinal ends of the absorbent structure, is changed as a result of pressure being applied to the binder fibers while the binder fibers are heated to a generally molten or otherwise activated state. For example, in typical molding operations, the absorbent structure or at least one or both major faces of the absorbent structure is pressed against or within a mold during or after heating of the binder fibers, or the mold itself may be heated so as to heat the binder fibers. Such a molding process forces a reorientation of the absorbent structure fibers to a generally non-random orientation and, and may also re-shape or even emboss the major surfaces of the absorbent structure. Because the absorbent structure 101 remains unmolded during and after activation of the binder fibers, the orientation of fibers within the absorbent structure, including at the major faces, side edges and longitudinal ends thereof, remains generally random during and after activation of the binder fibers to stabilize the absorbent structure.

Following stabilization of the absorbent structure 101, the structure may have substantially the same shape, contour, material distribution and other characteristics as the pre-stabilized absorbent structure. The stabilized absorbent structure 101 is desirably sufficiently strong to support a peak tensile load which is at least a minimum of about 100 grams per inch (g/inch) of cross-directional (Y-axis) width of the absorbent structure. The stabilized absorbent structure 101 strength can alternatively be at least about 200 g/inch, and can optionally be at least about 500 g/inch. In other aspects, the absorbent structure 101 strength can be up to a maximum of about 10,000 g/inch, or more. The strength can alternatively be up to about 5000 g/inch, and can optionally be up to about 2000 g/inch. In determining the strength of the stabilized absorbent structure 101, any previously formed, separately provided reinforcing component should be excluded from the determination. Such reinforcing components (not shown) may, for example, be provided by a scrim, a continuous filament fiber, a yarn, an elastic filament, a tissue, a woven fabric, a non-woven fabric, an elastic film, a polymer film, a reinforcing substrate, or the like, as well as combinations thereof.

The stabilized absorbent structure 101 can be configured to have a strength sufficient to support a peak tensile load which is significantly greater than the peak tensile load that can be supported by the absorbent structure prior to activation of the binder fibers. In a particular aspect, the absorbent structure 101 can be configured to have sufficient strength to support a peak tensile load which is at least about 100% greater than the peak tensile load that can be supported by the absorbent structure prior to activation of the binder fibers. The stabilized structure 101 can alternatively be configured to support a peak tensile load which is at least about 200% greater. Optionally, the stabilized structure 101 can be configured to support a peak tensile load which is at least about 300% greater. The percentage of increase in the supported peak-load can be determined by the formula:

$$100*(F2-F1)/F1;$$

where:

F1=the peak tensile load that can be supported by the absorbent structure 101 prior to activation of the binder fibers; and F2=the peak tensile load that can be supported by the stabilized absorbent structure.

The peak load that can be supported by an absorbent structure 101 can be determined by employing TAPPI Test Method Number T 494 om-96 entitled "Tensile Properties of Paper and Paperboard" (using constant rate of elongation apparatus) dated 1996. The test sample has a width of 1 inch (2.54 cm), and a length of 6 inch (15.24 cm). The jaws used were INSTRON part number 2712-001 (available from Sintech, Inc., a business having offices in Research Triangle Park, N.C., U.S.A.), and were arranged with an initial separation distance of 5 inch (12.7 cm). The cross-head speed was 12.7 mm/min, and the testing employed a MTS Systems Corp. model RT/1 testing machine controlled by TESTWORKS version 4.0 software, which are available from MTS Systems Corp., a business having office in Eden Prairie, Minn., USA. Substantially equivalent equipment may optionally be employed.

The fluid permeability of the absorbent structure 101 is also affected by the incorporation of binder fibers therein to stabilize the absorbent structure. The fluid permeability is defined by Darcy's Law and is measured for an absorbent saturated with a particular amount of fluid. More particularly, the permeability as that term is used herein is determined by the following permeability test.

Permeability Test

Figure 11:
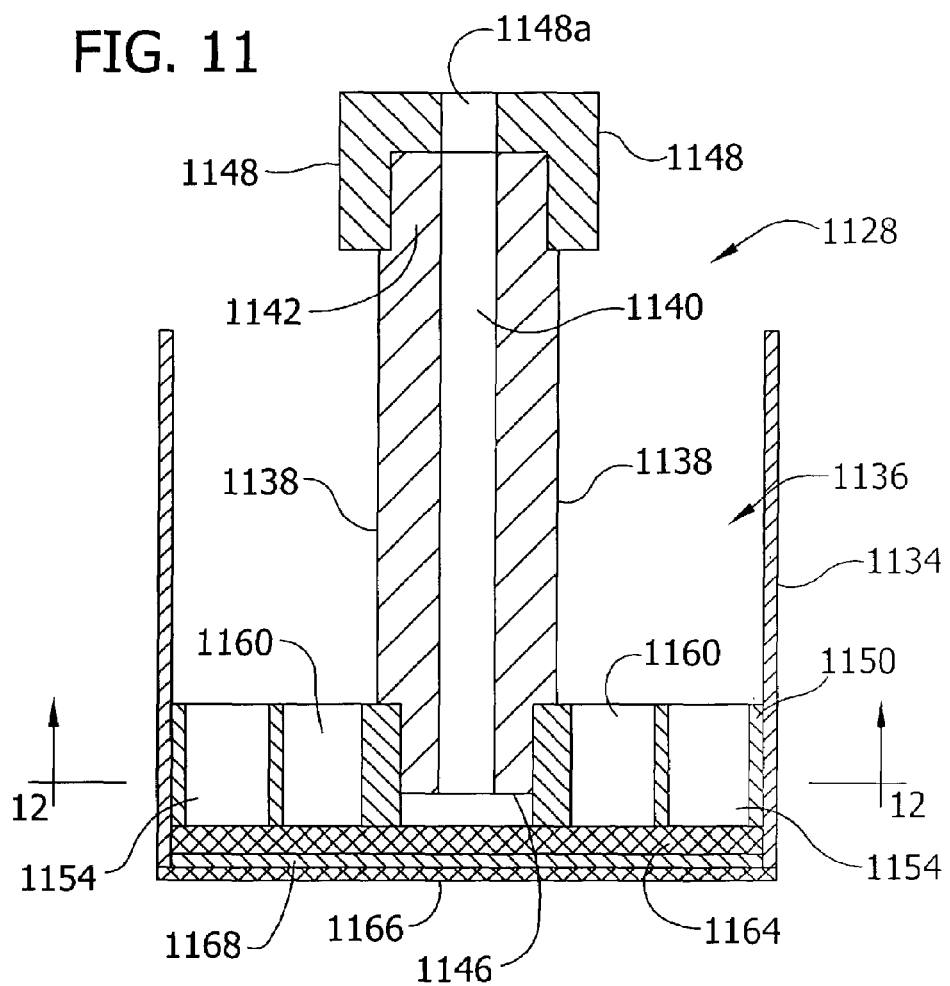
FIG. 11 is a cross-section of a permeability test apparatus.
Figure 12:
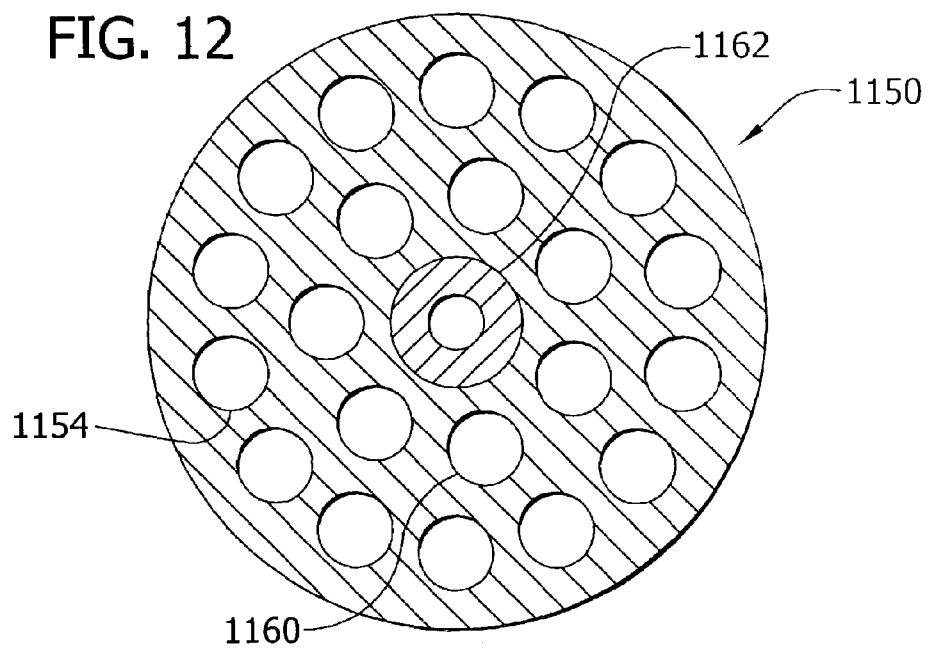
FIG. 12 is a cross-section taken in the plane of line 12-12 of FIG. 11.

A suitable permeability test apparatus is shown in FIGS. 11 and 12. The test apparatus comprises a cylinder 1134 and piston, generally indicated at 1136. The piston 1136 comprises a cylindrical LEXAN shaft 1138 having a concentric cylindrical hole 1140 bored down the longitudinal axis of the shaft. Both ends of the shaft 1138 are machined to provide ends 1142, 1146. A weight, indicated as 1148, rests on one end 1142 and has a cylindrical hole 1148a bored through at least a portion of its center. A circular piston head 1150 is positioned on the other end 1146 and is provided with a concentric inner ring of seven holes 1160, each having a diameter of about 0.95 cm, and a concentric outer ring of fourteen holes 1154, also each having a diameter of about 0.95 cm. The holes 1154, 1160 are bored from the top to the bottom of the piston head 1150. The piston head 1150 also has a cylindrical hole 1162 bored in the center thereof to receive end 1146 of the shaft 1138. The bottom of the piston head 1150 may also be covered with a biaxially stretched stainless steel screen 1164 with square openings of about 149 microns. A representative material for this piston is part number 85385T972 from McMaster-Carr Supply, a company having offices in Chicago, Ill., U.S.A.

Attached to the bottom end of the cylinder 1134 is a stainless steel cloth screen 1166 that is biaxially stretched to tautness prior to attachment. The screen 1166 has square openings of about 105 microns. A representative material for the screen is part number 85385T976 from McMaster-Carr Supply, company having offices in Chicago, Ill., U.S.A. A sample of the composite indicated as 1168 is supported on screen 1166.

The cylinder 1134 is either bored from a transparent LEXAN rod or equivalent or cut from a LEXAN tubing or equivalent and has an inner diameter of about 6.00 cm and a height of approximately 10 cm. The cylinder includes a set of drainage holes (not shown) or other suitable means for holding a fluid level in the cylinder at approximately 7.8 cm above the screen 1166. Piston head 1150 is machined from a LEXAN rod or equivalent. It has a height of approximately 16 mm and a diameter sized such that it fits within the cylinder 1134 with minimum wall clearance but still slides freely. Hole 1162 in the center of the piston head 1150 is used to match and provide snug, fluid impervious attachment to shaft end 1146. Shaft 1138 is machined from a LEXAN rod or equivalent and has an outer diameter of about 2.32 cm and an inner diameter of about 0.64 cm. End 1146 is approximately 2.54 cm long and approximately 1.52 cm in diameter, forming an annular shoulder to support the weight 1148. The annular weight 1148 has an inner diameter of about 1.59 cm so that it slips onto end 1142 of the shaft 1138 and rests on the annular shoulder formed therein. The annular weight can be made from a stainless steel or form other materials with corrosion resistance to 0.9% isotonic saline solution. The combined weight of the piston 1136 and weight 1148 equals approximately 596 g, which correspond to a pressure of about 20.7 dynes/cm²) on an area of 28.27 cm².

When solutions flow through the piston/cylinder apparatus, the cylinder 1134 generally rests on a 16 mesh rigid stainless steel support screen (not shown). Alternatively, the piston/cylinder arrangement may rest on a support ring (not shown) which matches the walls of the cylinder but effectively does not restrict flow from the bottom of the cylinder.

The piston and weight are placed in an empty cylinder to obtain a measurement from the bottom of the weight to the top of the cylinder. This measurement is taken using a caliper readable to 0.01 mm. Alternatively, this measurement is taken using a bulk gauge with 0.01 mm accuracy such as a Model IDF-1050E gauge available from Mitutoyo America Corporation, a company having offices in Aurora, Ill., U.S.A. This measurement will later be used to calculate the height of the gel bed. It is important to measure each cylinder empty and to keep track of which piston and weight used. The same piston and weight should be used for measurement when the absorbent structure sample is swollen.

The absorbent structure sample used for determining permeability is formed by swelling a circular sample (e.g., a cutout) of approximately 60 mm diameter placed in the bottom of the permeability cup apparatus (the sample should be in contact with the screen) with 0.9% (w/v) aqueous NaCl for a time period of about 60 minutes. The saline would be placed in a tray. A coarse plastic or rubber mesh with uniform square openings of approximately 2-15 mm is used to allow saline to reach the cups to swell the samples.

At the end of this period, the piston and weight are placed on the swollen sample in the cylinder and then the cylinder, piston, weight, and sample are removed intact from the saline. The thickness of the swollen sample is determined by measuring from the bottom of the weight to the top of the cylinder with a micrometer. Alternatively, this measurement is taken using a bulk gauge with 0.01 mm accuracy such as a Model IDF-1050E gauge available from Mitutoyo America Corporation, a company having offices in Aurora, Ill., U.S.A., provided that the zero point is unchanged from the initial thickness test. The thickness value obtained from measuring the empty cylinder, piston, and weight is subtracted from the value of the thickness obtained after swelling the absorbent structure. The resulting value is the height "H" of the swollen sample.

The absorbent structure permeability measurement is initiated by adding the NaCl solution to cylinder 1134 with swollen sample 1168, piston 1150, and weight 1148 inside. The 0.9% NaCl solution is added to achieve and maintain a fluid height of about 7.8 cm above the bottom of the swollen absorbent structure sample. The quantity of fluid passing through the swollen sample versus time is measured gravimetrically. Data points are collected every second for thirty seconds once the fluid level has been stabilized to and maintained at about 7.8 cm in height. The flow rate Q through the swollen sample 1168 is determined in units of gm/sec by a linear least-square fit of fluid passing through the sample 1168 (in grams) versus time (in seconds).

Permeability in square microns is obtained by the following equation:

$$K=[Q*H*Mu*10^8]/[A*Rho*P]$$

where K=Permeability (square microns), Q=flow rate (g/sec), H=height of swollen absorbent structure sample (cm), Mu=liquid viscosity (poise), A, =cross-sectional area for liquid flow (cm²), Rho=liquid density (g/cm³), and P=hydrostatic pressure (dynes/cm²). The hydrostatic pressure is calculated from $$P=Rho*g*h$$

where Rho=liquid density (g/cm³), g=gravitational acceleration, nominally 981 cm/sec², and h=fluid height, e.g., 7.8 cm for the permeability test apparatus described above.

In general, the higher the permeability of the absorbent structure when saturated, the more open the structure is. As a result, the absorbent structure can more easily take in additional fluid and is therefore less likely to leak. Without binder material, the permeability of a non-woven absorbent structure is based solely on the characteristics of the absorbent fibers and superabsorbent material and therefore has a relatively low fluid permeability, such as less than 20 square microns. The integrity of the absorbent structure 101, and more particularly the void volume thereof, is increased by stabilizing the structure with binder materials, and more particularly by multi-component binder fibers, to substantially increase the permeability of the absorbent structure. For example, following activation of the binder fibers, the stabilized absorbent structure 101 desirably has a permeability throughout the absorbent structure as measured by the above permeability test of greater than 20 square microns, more desirably greater than about 40 square microns, and even more desirably greater than about 60 square microns.

It is understood that the permeability may be non-uniform along at least one of the length and the width of the absorbent structure 101, as long as the local permeability of the absorbent structure is at least greater than 20 square microns. Without being bound to theory, it is also believed that an over-concentration of binder fibers within the stabilized absorbent structure can negatively affect the permeability of the absorbent structure. To facilitate increased permeability of the absorbent structure, the binder fiber concentration within the absorbent structure is desirably in the range of about 0.1 percent to about 10 percent, and more desirably in the range of about 0.1 percent to about 5 percent, to facilitate increased permeability of the absorbent structure.

Where the binder fibers are activated by subjecting the pre-stabilized absorbent structure 101 to dialectric heating (e.g., by exposure to electromagnetic energy), the stabilized absorbent structure also has unique physical characteristics associated with the presence of the binder fibers and subsequent activation by electromagnetic energy. These characteristics may be qualified and quantified using measurements of location and degree of oxidation and bonding efficiency within the absorbent structure. More particularly, techniques such as ultraviolet, visible, near infrared, infrared and Raman spectroscopy; surface analysis; differential scanning calorimetry; chromatographic separation; and various microscopic techniques can demonstrate the unique properties of materials heated "externally" via convection or infrared radiant heat transfer, versus "internally" using dielectric techniques.

With infrared and convection heating, radiant energy is translated into heat at the outer surface of the absorbent structure where the surface temperature rises rapidly. Heat at the outer surface of the absorbent structure eventually diffuses via thermal conduction toward the center of the absorbent structure. This heating process is relatively slow and it takes a relatively significant time for the center of the absorbent structure to reach the threshold temperature necessary to melt binder fibers disposed toward the center of the structure. The slow process of thermal conduction is dependent upon the thermal conductivity of the structure and its overall dimensions (e.g., thickness). For such a heating process, a greater oxidation of fibers consequently occurs toward, and more particularly on, the outer surface of the structure. Thermal bonding in this manner also results in some yellowing of the fibers at the outer surface of the absorbent structure.

For dielectric heating (e.g., using electromagnetic energy), the peak temperature of the absorbent structure 101 is also near the outer surface. However, the temperature rise at the center of the absorbent structure 101 is nearly identical to that at the outer surface. This occurs since the dielectric heating process is active and direct. This direct transfer of energy to the center of the absorbent structure is less dependent upon thermal conductivity and more dependent upon the dielectric field strength and dielectric properties of the absorbent structure materials. In other words, the heating occurs generally from the center of the absorbent structure 101 out toward the outer surface thereof.

Infrared energy must be applied from about 3 to 30 times longer than dielectric heating to achieve generally uniform heating throughout the absorbent structure. More particularly, such an extended heating time is required in order to attain a desired temperature threshold (e.g., the melting temperature of the binder fiber) at the center of the absorbent structure. When properly applied, dielectric heating occurs rapidly and more uniformly. The rapid and uniform direct heating prevents large-scale thermal degradation of polymers within the heated absorbent structure.

The percent oxidation occurring for any given structure is proportional to the time exposure of the polymer to air at an elevated temperature (i.e., above 75° C.). Infrared heating maintains a higher surface temperature throughout the heating cycle than microwave heating. The projected percent oxidation from infrared and convection heating will be from 5 to 35 (or more) times greater at the outer surface of an absorbent structure than it would be at the outer surface of an structure subjected to dielectric heating. Heating an absorbent structure by microwave radiation will, therefore, produce a structure having less than 5 times more oxidation at its outer surface than at its center and more particularly less than 3 times more oxidation at its outer surface than at its center.

Large differences in oxidative degradation due to surface heating are easily measured using the analytical techniques previously described. For this application, typical compounds resulting from oxidative degradation include the existence of highly colored (high molar absorptivity) species. These colored compounds result from the formation of identifiable unsaturation. Examples include polyenes, unsaturated ketones, carboxyl-containing organic chains, quinones, and in general compounds with conjugated double bonds formed by the oxidation/degradation mechanisms of free radical formation, elimination reactions, and random chain scission. Often the increased oxidation can readily be observed with the unaided eye, making the materials heated using infrared and convection heating appear more yellow and thus of perceived lower quality.

A rapid, non-destructive method to analyze polyolefins and cellulosic materials for the presence of compounds resulting from thermal degradation is hereafter described. The ultraviolet and visible spectrum is measured on a control and heated sample. The resulting spectra are subtracted and the difference spectra compared to a series of reference sample spectra prepared by heating a series of comparison samples at elevated temperatures for different known periods to bracket the heating application. The spectra yield direct information on the color and molecular absorptive properties of the thermal degradation products present in polymers and cellulose. The ratios of the absorbance maximum for the ultraviolet versus the visible spectrum yields precise information on the chemical species present and on the approximate concentrations. This basic procedure can be reproduced using ultraviolet and visible fluorescence, Raman spectroscopy, and infrared spectroscopy for similar and complementary results.

For more detailed structural analysis, the polymer and cellulosic materials can be dissolved in appropriate solvents, subjected to liquid chromatographic separation, and further analyzed using either the spectroscopic techniques described above or by mass spectrometry to determine the structure and molecular weight of any degradation compounds. These compounds are often highly colored as yellow or brown due to the browning effect of thermal degradation oxidation. There is a plethora of literature describing the detailed analysis of degradation compounds in synthetic and natural polymers and most of these techniques are quite sufficient for measuring the relative amount of oxidation throughout the cross-section of the heated structure. In addition, the use of scanning electron microscopy with osmium tetroxide staining will reveal the integrity of bond points within the structure indicating the maximum heating temperature reached in any portion of the heated structure during the process.

FIGS. 5-10 illustrate one embodiment of apparatus, generally indicated at 121, for making a stabilized absorbent structure 101 in accordance with the present invention and the above-described method. The apparatus 121 has an appointed lengthwise or machine-direction 123, an appointed widthwise or cross-direction 125 which extends transverse to the machine direction, and an appointed thickness or z-direction 127. For the purposes of the present disclosure, the machine-direction 123 is the direction along which a particular component or material is transported lengthwise or longitudinally along and through a particular, local position of the apparatus. The cross-direction 125 lies generally within the plane of the material being transported through the process, and is aligned perpendicular to the local machine-direction 123. The z-direction 127 is aligned substantially perpendicular to both the machine-direction 123 and the cross-direction 125, and extends generally along a depth-wise, thickness dimension. In the illustrated embodiment, the machine direction 123 corresponds to the longitudinal X-axis of the diaper 21 of FIG. 1 and the cross-direction 125 corresponds to the lateral Y-axis of the diaper.

Figure 5:
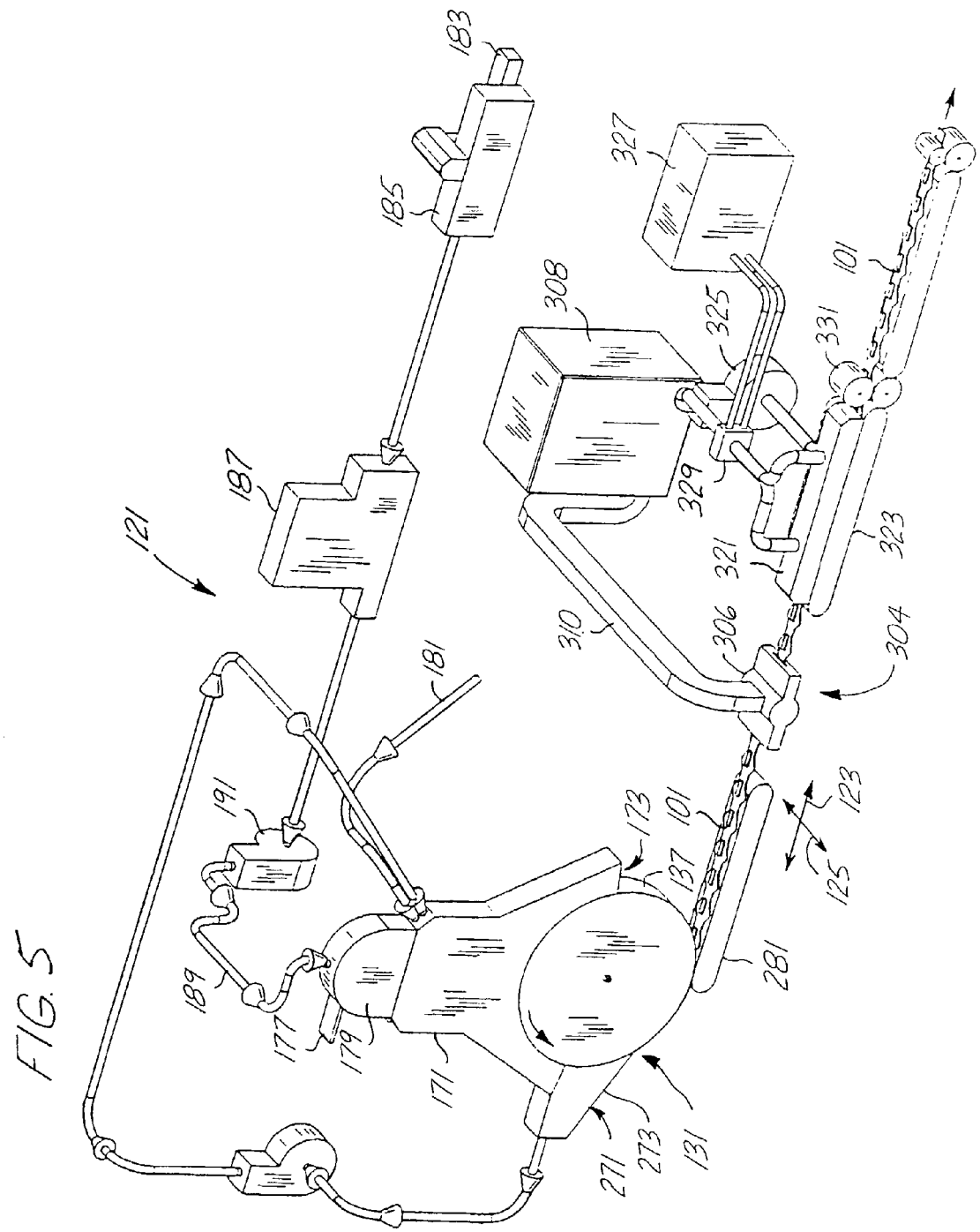
FIG. 5 is a schematic perspective of apparatus for forming an absorbent structure of the present invention.
Figure 6:
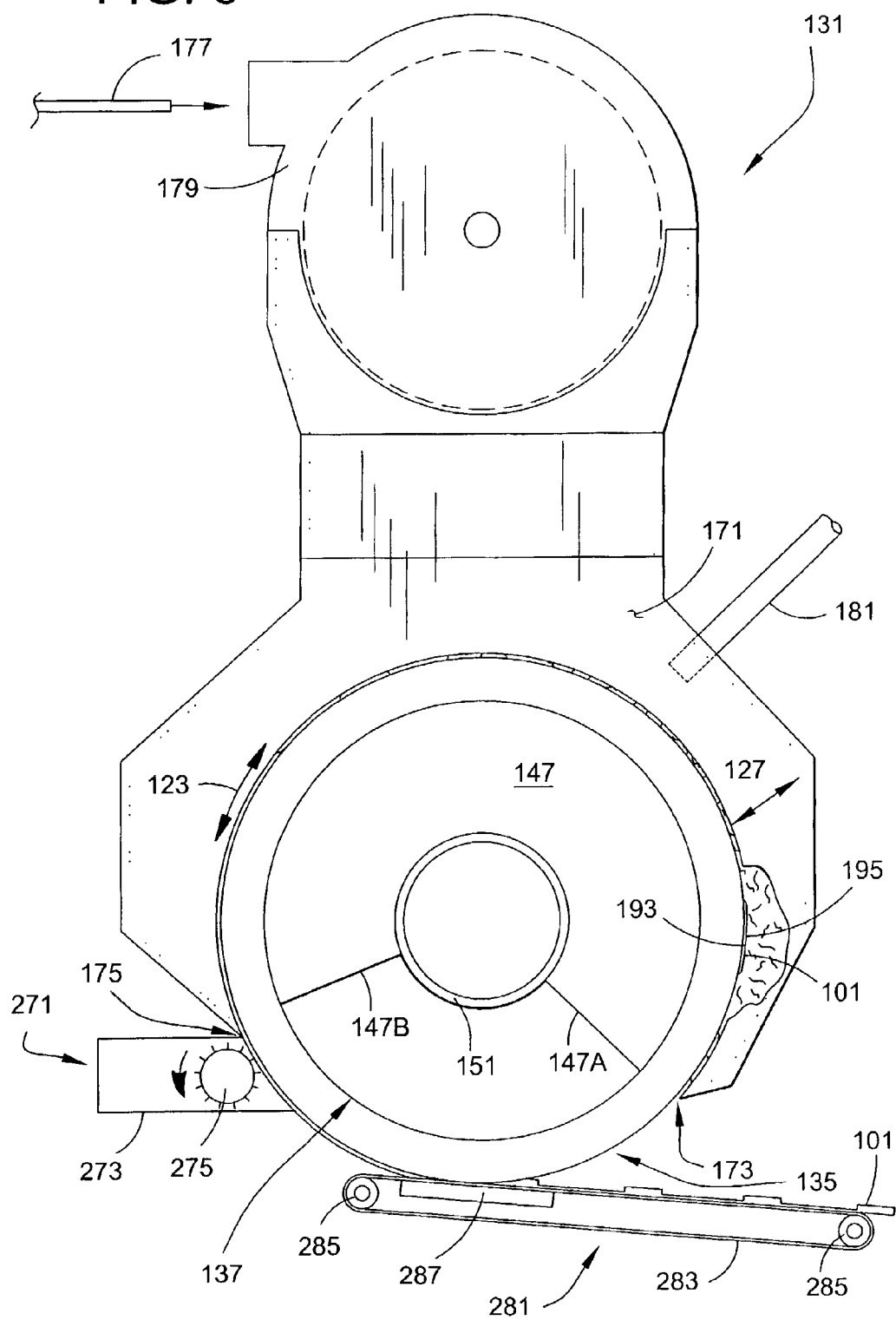
FIG. 6 is an enlarged side elevation of an airforming device of the apparatus of FIG. 5.
Figure 7:
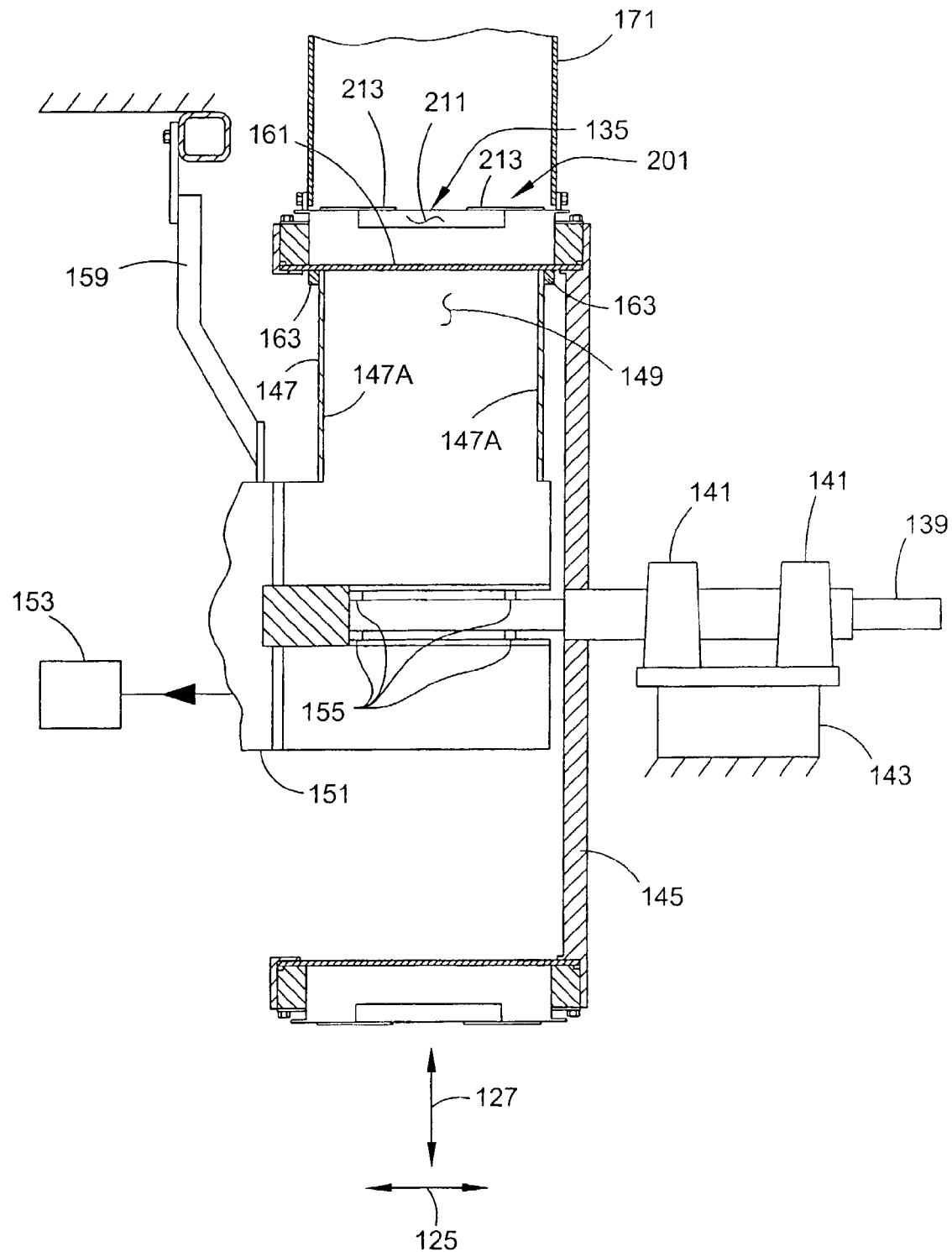
FIG. 7 is a fragmentary cross-section of the airforming device of FIG. 6.

The apparatus 121 comprises an airforming device, generally indicated at 131 in FIGS. 5 and 6, having a movable, foraminous forming surface 135 extending about the circumference of a drum 137 (the reference numerals designating their subjects generally). The drum 137 is mounted on a shaft 139 (FIG. 7) connected by bearings 141 to a support 143. As shown in FIG. 7, the drum includes a circular wall 145 connected to the shaft 139 for conjoint rotation therewith. The shaft 139 is rotatably driven by a suitable motor or line shaft (not shown) in a counter-clockwise direction in the illustrated embodiment of FIGS. 5 and 6. The circular wall 145 cantilevers the forming surface 135 and the opposite side of the drum 137 is open. A vacuum duct 147 located radially inward of the forming surface 135 extends over an arc of the drum interior. The vacuum duct 147 has an arcuate, elongate entrance opening 149 under the foraminous forming surface 135, as will be described in more detail hereinafter, for fluid communication between the vacuum duct and the forming surface. The vacuum duct 147 is mounted on and in fluid communication with a vacuum conduit 151 connected to a vacuum source 153 (represented diagrammatically in FIG. 7). The vacuum source 153 may be, for example, an exhaust fan.

The vacuum duct 147 is connected to the vacuum supply conduit 151 along an outer peripheral surface of the conduit and extends circumferentially of the conduit. The vacuum duct 147 projects radially out from the vacuum conduit 151 toward the forming surface 135 and includes laterally spaced side walls 147A and angularly spaced end walls 147B. The shaft 139 extends through the wall 145 and into the vacuum supply conduit 151 where it is received in a bearing 155 within the conduit. The bearing 155 is sealed with the vacuum supply conduit 151 so that air is not drawn in around the shaft 139 where it enters the conduit. The brace 157 and entire conduit 21 are supported by an overhead mount 159.

A drum rim 161 (FIG. 7) is mounted on the wall 145 of the drum 137 and has a multiplicity of holes over its surface area to provide a substantially free movement of fluid, such as air, through the thickness of the rim. The rim 161 is generally tubular in shape and extends around the axis of rotation of the shaft 139 near the periphery of the wall 145. The rim 161 is cantilevered away from the drum wall 145 and has a radially inward-facing surface positioned closely adjacent to the entrance opening 149 of the vacuum duct 147. To provide an air resistant seal between the rim 161 and the entrance opening 149 of the vacuum duct 147, rim seals 163 are mounted on the inward-facing surface of the rim 161 for sliding, sealing engagement with the walls 147A of the vacuum duct. Seals (not shown) are also mounted on the end walls 147B of the vacuum duct 147 for sliding, sealing engagement with the inward-facing surface of the rim 161. The seals may be formed of a suitable material such as felt to permit the sliding, sealing engagements.

Referring back to FIG. 6, the apparatus 121 further comprises a forming chamber 171 through which the forming surface 135 is movable conjointly with the drum 137 upon rotation thereof. More particularly, in the illustrated embodiment the forming surface 135 moves in a counter-clockwise direction within the forming chamber 171 generally from an entrance 173 through which the forming surface enters the forming chamber substantially free of fibrous material, and an exit 175 through which the forming surface exits the forming chamber with the pre-stabilized absorbent structure 101 formed thereon. Alternatively, the drum 137 may rotate in a clockwise direction relative to the forming chamber 171. The forming chamber 171 is supported by a suitable support frame (not shown) which may be anchored and/or joined to other suitable structural components as necessary or desirable.

An absorbent fiber material, such as in the form of a batt 177 (FIGS. 5 and 6) of absorbent fibers, is delivered from a suitable supply source (not shown) into a fiberizer 179, which may be a conventional rotary hammer mill, a conventional rotatable picker roll or other suitable fiberizing device. The fiberizer 179 separates the batt 177 into discrete, loose absorbent fibers which are directed from the fiberizer into the interior of the forming chamber 171. In the illustrated embodiment, the fiberizer 179 is disposed above the forming chamber 171. However, it is to be understood that the fiberizer 179 may instead be located remote from the forming chamber 171 and that absorbent fibers may be delivered to the interior of the forming chamber in other ways by other suitable devices and remain within the scope of the present invention.

Particles or fibers of superabsorbent material may be introduced into the forming chamber 171 by employing conventional mechanisms such as pipes, channels, spreaders, nozzles and the like, as well as combinations thereof. In the illustrated embodiment, superabsorbent material is delivered into the forming chamber 171 via a delivery conduit 181 and nozzle system (not shown). A binder fiber material is delivered from a suitable binder fiber supply 183, such as in the form of bales (not shown), to a suitable opening device 185 to generally separate the binder fiber material into discrete, loose binder fibers. For example, the opening device 185 may be suitable for picking, carding, planing or the like, as well as combinations thereof.

Selected quantities of binder fiber are then directed to a metering device 187, and the metering device feeds controlled quantities of the binder fiber into a binder fiber delivery conduit 189. As an example, the binder fiber metering device 187 may be a model number CAM-1X12 device which is available from Fiber Controls, Inc., a business having offices located in Gastonia, N.C., U.S.A. A blower 191 or other suitable device may be employed to help the flow of binder fibers through the delivery conduit 189.

In the illustrated embodiment, the binder fiber conduit 189 delivers the binder fibers into the fiberizer 171 for generally homogenous mixing with the absorbent fibers such that a homogenous mixture of absorbent and binder fibers is subsequently delivered into the forming chamber 171. However, it is understood that the binder fibers may instead be delivered into the interior of the forming chamber 171 separate from the absorbent fibers, and at a location other than at the delivery point at which the absorbent fibers are directed by the fiberizer 179 into the forming chamber.

Where the binder fibers are directed into the forming chamber 171 at a location which is closer to the entrance 173 of the forming chamber, the binder fibers will be more concentrated toward an inner or forming surface side 193 (FIG. 6) or major face of the absorbent structure 101 formed on the forming surface 135. Where the binder fibers are directed into the forming chamber 171 at a location which is closer to the exit 175 of the forming chamber, the binder fibers will be more concentrated toward an outer or free-surface side 195 (FIG. 6) or major face of the absorbent structure 101. As an alternative, the binder fibers may be combined with or otherwise incorporated into the source of the absorbent fibers instead of being separately delivered to the airforming device 131. For instance, the binder fibers may be blended with the absorbent fibers before the absorbent fibers are formed into a supply roll (e.g. the batt 177).

The foraminous forming surface 135 is defined in the illustrated embodiment by a series of mold elements, or form members 201 which are arranged end-to-end around the periphery of the forming drum 137 and independently attached to the drum. As may be seen in FIG. 8, the form members 201 each define a substantially identical pattern in which fibrous material is collected. The patterns correspond to a desired length, width and thickness of individual absorbent structures 101 which repeats over the circumference of the drum 137. However, partially repeating or non-repeating pattern shapes may be used with the present invention. It is also understood that a continuous, un-patterned absorbent structure may be formed on the forming surface 135, such as where the forming surface is flat or where the formed absorbent structure is generally rectangular, and is subsequently processed (e.g., cut or otherwise formed) to a desired shape.

Figure 8:
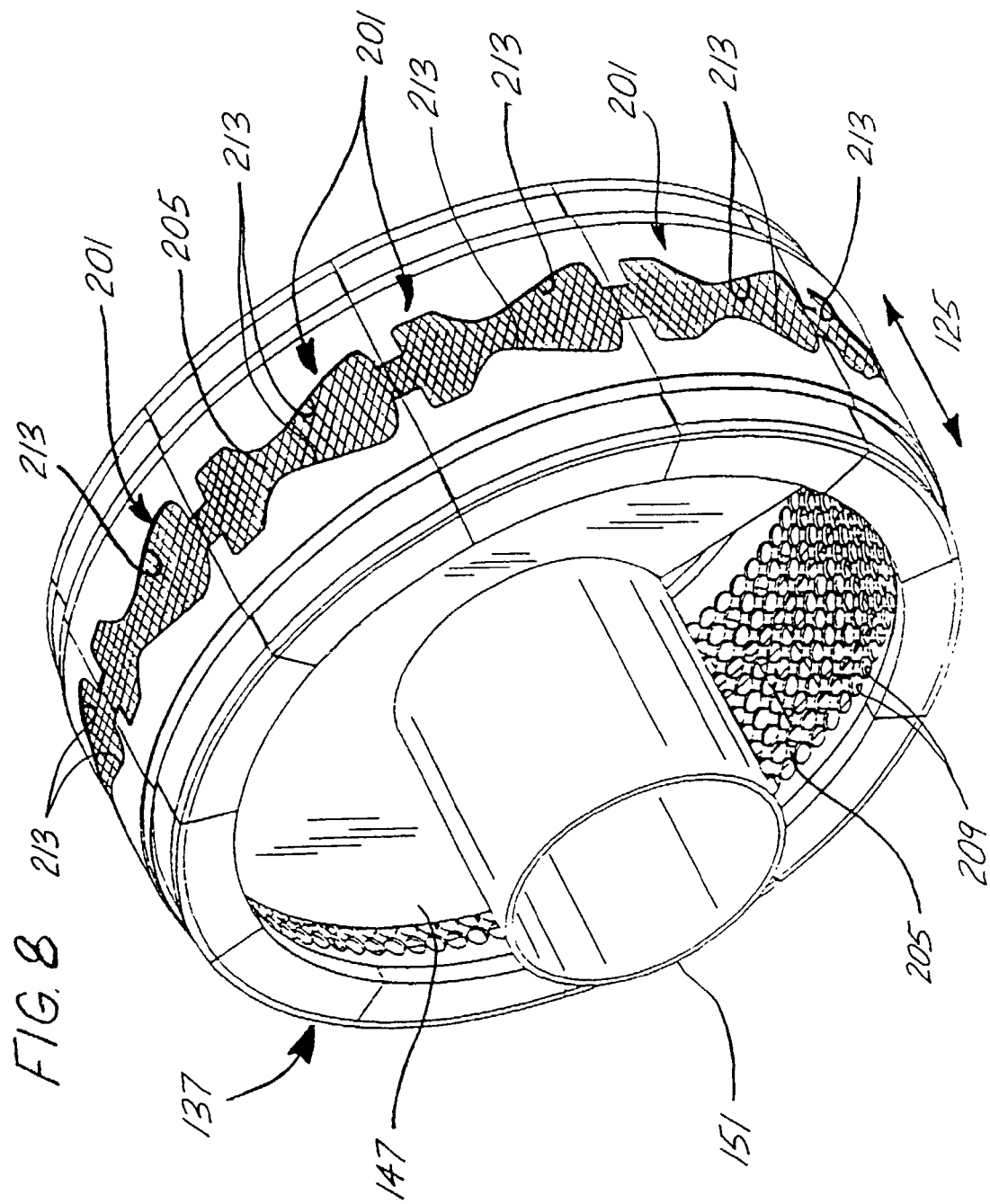
FIG. 8 is a schematic perspective of a forming drum and forming surface of the airforming device of FIG. 6.
Figure 9:
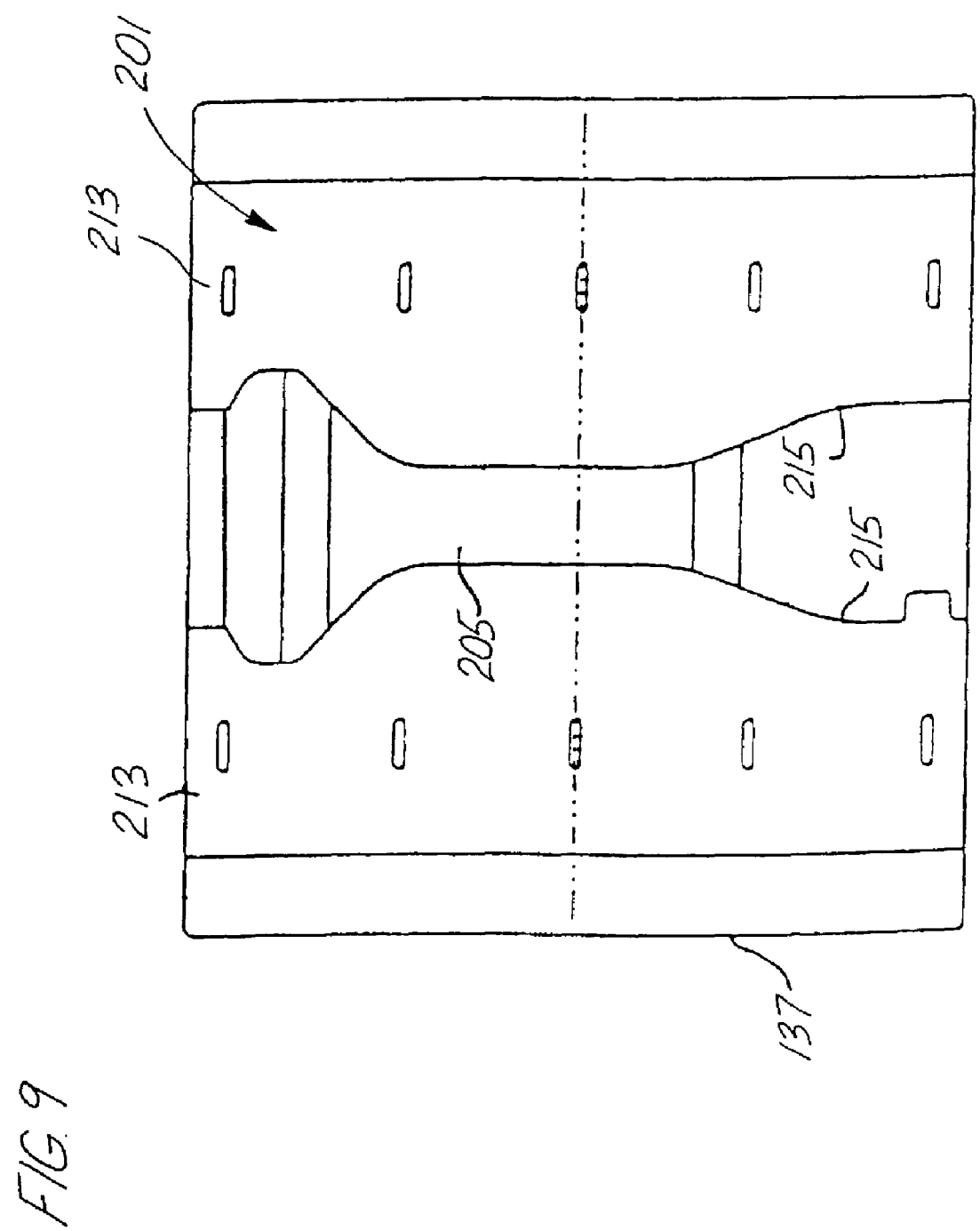
FIG. 9 is an enlarged schematic of a portion of the forming drum and forming surface.
Figure 10:
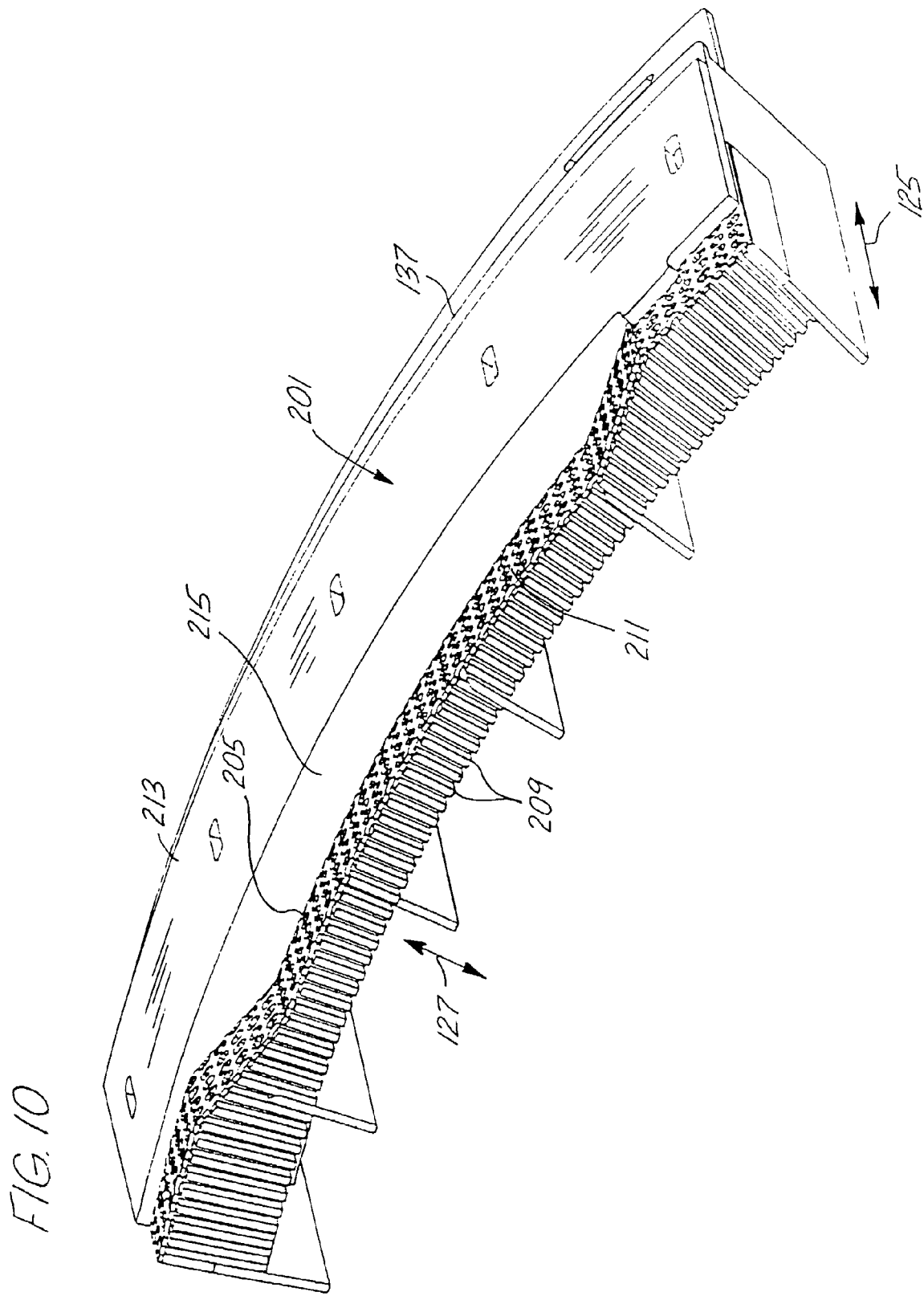
FIG. 10 is a schematic perspective of a longitudinal cross-section taken through a portion of the forming drum and forming surface.

With general reference now to FIGS. 8-10, the form members 201 comprise a foraminous member 205 which is operatively located on and secured to the forming drum 135. The foraminous member 205 may include a screen, a wire mesh, a hard-wire cloth, a perforated member or the like, as well as combinations thereof. In the particular embodiment shown in FIG. 10, the foraminous member 205 is fluted to define open channels 209 which extend generally radially to allow a substantially free flow of air or other selected gas from the outer surface of the drum 137 toward the interior of the drum. The channels 209 can have any desired cross-sectional shape, such as circular, oval, hexagonal, pentagonal, other polygonal shape or the like, as well as combinations thereof.

With particular reference to FIG. 10, the radially outermost surface defined by the foraminous member 205 can be configured with a non-uniform depth-wise (e.g., z-direction 127) surface contour to provide a desired non-uniform thickness of the pre-stabilized absorbent structure 101 formed on the forming surface 135. In desired arrangements, the z-direction 127 variation of the surface contour can have a selected pattern which may be regular or irregular in configuration. For example, the pattern of the surface contour can be configured to substantially provide a selected repeat-pattern along the circumferential dimension of the forming drum 137.

The surface contour of the foraminous member 205 shown in FIG. 10 thus defines longitudinally opposite end regions having a first average depth and a central region having a second average depth that is greater than the first average depth. Each end region with the first average depth can provide a lower-basis-weight region and/or thickness of the absorbent structure 101 formed on the forming surface 135, and the central region with the greater second average depth can provide a relatively higher-basis-weight and/or thickness region of the absorbent structure. Desirably, each region with the first average depth can be substantially contiguous with an adjacent region with the greater second depth. It is also understood that the foraminous member 205 may be configured to have a z-direction 127 surface contour across the width of the forming surface 135 for providing a non-uniform basis weight and/or thickness across the width of the absorbent structure 101 formed on the forming surface.

In desired arrangements, the surface contour of the foraminous member 205 defines a generally trapezoidal shape. Alternatively, the contour may define a domed shape or may be flat. In the illustrated embodiment, the depth profile defined by the foraminous member 205 forms a pocket region 211 extending in the machine direction 123 along a portion of the length of the forming surface 135 and across a central portion of the width thereof for forming the absorbent structure shown in FIG. 4.

In a further aspect, one or more non-flow regions of the forming surface may be formed by employing a suitable blocking mechanism (not shown) which covers or otherwise occludes the flow of air through selected regions of the forming surface 135. As a result, the blocking mechanism can deflect or reduce the amount of fibers deposited on the areas of the forming surface 135 covered by the blocking mechanism. The blocking mechanism can optionally be configured to form other desired features of the absorbent structure 101, such as a series of key notches (not shown) on the formed absorbent structure. The key notches can, for example, provide a sensing point for locating and positioning a subsequent severing of a web of longitudinally connected absorbent structures 101 formed on the forming surface 135 into discrete absorbent structures.

Still referring to FIGS. 8-10, the form members 201 can also include one or more side-masking members 213, also sometimes referred to as contour rings, configured to provide a desired shape (e.g., width profile) to the absorbent structure 101. For example, in the illustrated embodiment the side-masking members 213 are provided by a pair of laterally opposed ring members which extend circumferentially around the forming drum 137 in laterally (cross-direction 125) opposed relationship with each other. Each of the members 213 has a non-uniform inner side wall 215 along its respective length so that the laterally opposed inner side walls of the side-masking members 213 define the width profile of the absorbent structure 101 formed on the forming surface 135. More particularly, the inner side walls 215 of the side-masking members 213 have a generally serpentine contour as they extend in the machine direction 123. As a result, the side-masking members 213 provide alternating narrower and wider regions of the form members 201. Accordingly, the absorbent structure 101 delivered from the airforming device 131 can have a width profile which is non-uniform along at least a portion of the length of the structure.

In another feature, at least one of the side-masking members 213 can include one or more key tabs (not shown). The individual key tabs may, for example, be employed for marking or otherwise identifying each intended absorbent structure 101 length along the circumference of the forming drum 137. Such side-masking members 213 can be particularly advantageous when the airforming device 131 is employed to produce absorbent structures for use in disposable, shaped absorbent articles, such as diapers, children's training pants, feminine care products, adult incontinence products and the like.

It is understood that the inner side walls 215 of the side-masking members 213 can instead be generally straight (e.g. parallel to the machine direction 123) to produce a substantially rectangular, ribbon shaped absorbent structure 101. It is also understood that the side edges 105 of the absorbent structure 101 can alternatively be provided by cutting and removal, cutting and folding, or the like, as well as combinations thereof.

While the forming surface 135 is illustrated herein as being part of the forming drum 137, it is to be understood that other techniques for providing the forming surface 135 may also be employed without departing from the scope of the present invention. For example, the forming surface 135 may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

In operation to make a formed, non-woven pre-stabilized absorbent structure, e.g., prior to activation of the binder fibers to form inter-fiber bonds within the absorbent structure, the vacuum source 153 (FIG. 7) creates a vacuum in the vacuum duct 147 relative to the interior of the forming chamber 171. As the forming surface 135 enters and then moves through the forming chamber 171 toward the exit 175 thereof, the absorbent fibers, binder fibers and superabsorbent material within the forming chamber are operatively carried or transported by an entraining air stream and drawn inward by the vacuum toward the foraminous forming surface. It is understood that the absorbent fibers, superabsorbent materials and binder fibers may be entrained in any suitable fluid medium within the forming chamber 171. Accordingly, any reference herein to air as being the entraining medium should be understood to be a general reference which encompasses any other operative entraining fluid. Air passes inward through the forming surface 135 and is subsequently passed out of the drum 137 through the vacuum supply conduit 151. Absorbent fibers, binder fibers and superabsorbent materials are collected by the form members 201 to thereby form the pre-stabilized absorbent structure 101.

It is understood that the level or strength of the vacuum suction can be selectively regulated to control the density of the absorbent structure 101 formed on the forming surface 135. A relatively greater suction strength can be employed to produce a relatively higher density, or low porosity, in the absorbent structure 101, and a relatively lower suction strength can be employed to produce a relatively lower density, or high porosity, in the absorbent structure. The specific level of suction strength will depend upon the specific flow characteristics present in the forming chamber 171. It is readily apparent that a desired suction strength can be found by employing a short, iterative series of well known trial steps. The density of the absorbent structure 101 prior to activation of the binder fibers can be important for controlling the desired functional properties of the subsequently stabilized absorbent structure.

Subsequently, the drum 137 carrying the absorbent structure 101 passes out of the forming chamber 171 through the exit 175 to a scarfing system, generally indicated at 271 in FIGS. 5 and 6, where excess thickness of the absorbent structure can be trimmed and removed to a predetermined extent. The scarfing system 271 includes a scarfing chamber 273 and a scarfing roll 275 positioned within the scarfing chamber. The scarfing roll 275 abrades excess fibrous material from the absorbent structure 101, and the removed materials are transported away from the scarfing chamber 273 within a suitable discharge conduit as is well known in the art. The removed fibrous material may, for example, be recycled back into the forming chamber 171 or the fiberizer 179, as desired. Additionally, the scarfing roll 275 can rearrange and redistribute the fibrous material along the machine-direction 123 of the absorbent structure 101 and/or along the lateral or cross-machine direction 125 of the absorbent structure.

The rotatable scarfing roll 275 is operatively connected and joined to a suitable shaft member (not shown), and is driven by a suitable drive system (not shown). The drive system may include any conventional apparatus, such as a dedicated motor, or a coupling, gear or other transmission mechanism operatively connected to the motor or drive mechanism used to rotate the forming drum 137. The scarfing system 271 can provide a conventional trimming mechanism for removing or redistributing any excess thickness of the absorbent structure 101 that has been formed on the forming surface 135. The scarfing operation can yield an absorbent structure 101 having a selected contour on a major face-surface thereof (e.g., the free surface side 193 in the illustrated embodiment) that has been contacted by the scarfing roll 275. For example, the scarfing roll 275 may be configured to provide a substantially flat surface along the scarfed surface of the absorbent structure 101, or may optionally be configured to provide a non-flat surface. The scarfing roll 275 is disposed in spaced adjacent relationship with the forming surface 135, and the forming surface is translated past the scarfing roll upon rotation of the drum 137.

The scarfing roll 275 of the illustrated embodiment rotates in a clockwise direction which is counter to the direction of rotation of the drum 137. Alternatively, the scarfing roll 275 may be rotated in the same direction as the forming surface 135 on the forming drum 137. In either situation, the rotational speed of the scarfing roll 275 should be suitably selected to provide an effective scarfing action against the contacted surface of the formed absorbent structure 101. In like manner, any other suitable trimming mechanism may be employed in place of the scarfing system 271 to provide a cutting or abrading action to the fibrous absorbent structure 101 by a relative movement between the absorbent structure and the selected trimming mechanism.

After the scarfing operation, the portion of the forming surface 135 on which the absorbent structure 101 is formed can be moved to a release zone of the apparatus 121 disposed exterior of the forming chamber 171. In the release zone, the absorbent structure 101 is drawn away from the forming surface 135 onto a conveyor, which is indicated generally at 281 in FIGS. 5 and 6. The release can be assisted by the application of air pressure from the interior of the drum 137. The conveyor 281 receives the formed absorbent structure 101 from the forming drum 137 and conveys the absorbent structure to a collection area or to a location for further processing (not shown). Suitable conveyors can, for example, include conveyer belts, vacuum drums, transport rollers, electromagnetic suspension conveyors, fluid suspension conveyors or the like, as well as combinations thereof.

In the illustrated embodiment, the conveyor 281 includes an endless conveyor belt 283 disposed about rollers 285. A vacuum suction box 287 is located below the conveyor belt 283 to draw the absorbent structure 101 away from the forming surface 135. The belt 283 is perforate and the vacuum box 287 defines a plenum beneath the portion of the belt in close proximity to the forming surface so that the vacuum within the vacuum box acts on the absorbent structure 101 on the forming surface 135. Removal of the absorbent structure 101 from the forming surface 135 can alternatively be accomplished by the weight of the absorbent structure, by centrifugal force, by mechanical ejection, by positive air pressure or by some combination thereof or by another suitable method without departing from the scope of this invention. As an example, in the illustrated embodiment, the absorbent structures 101 exiting the forming chamber are interconnected end-to-end to form a web or series of absorbent structures, each of which has a selected shape that substantially matches the shape provided by the corresponding form members 201 used to form each individual absorbent structure.

Referring now to FIG. 5, after the pre-stabilized absorbent structures 101 are transferred from the forming surface 135 to the conveyor 281, each absorbent structure is subsequently transported to an activation system 304 wherein the binder fibers are activated to form inter-fiber bonds within the absorbent structure. In one embodiment, the binder activation system 304 includes an activation chamber 306 through which each absorbent structure 101 passes, and a generator 308 for radiating electromagnetic energy within the activation chamber as each absorbent structure passes therethrough. For example, a suitable microwave generator 308 can produce an operative amount of microwave energy, and can direct the energy through a suitable wave-guide 310 to the activation chamber 306.

In one embodiment, the electromagnetic energy may be radio frequency (RF) energy having an RF frequency which is at least a minimum of about 0.3 megahertz (MHz). The frequency can alternatively be at least about 300 MHz, and can optionally be at least about 850 MHz. In other aspects, the frequency can be up to a maximum of about 300,000 MHz, or more. The frequency can alternatively be up to about 30,000 MHz, and can optionally be up to about 2,600 MHz. In a particular embodiment, the radio frequency is desirably about 27 MHz. In another embodiment, the electromagnetic energy may be microwave energy in the range of about 915 MHz to about 2450 MHz.

In a particular arrangement, the electromagnetic energy can operatively heat the binder fibers to a temperature above the melting point of the binder fiber material. The melted binder fibers can then adhere or otherwise bond and operatively connect to the absorbent fibers, to the superabsorbent material and/or to other binder fibers within the absorbent structure. The binder fibers may also be activated substantially without heating up the entire mass of the absorbent structure 101. In a particular feature, the binder fibers can be rapidly activated while substantially avoiding any excessive burning of the absorbent structure 101.

The heating and melt activation of the binder fibers can be produced by any operative mechanism available in the absorbent structure 101. For example, the electromagnetic energy may heat water vapor present within the absorbent structure 101, and the heated vapor can operatively melt the binder fibers. In another mechanism, the electromagnetic energy can be absorbed by the binder fibers and the absorbed energy can operatively heat and melt the binder fibers.

The total residence time of the absorbent structure 101 within the activation chamber 306 can provide a distinctively efficient activation period. In a particular aspect, the activation period can be at least a minimum of about 0.002 sec. The activation period can alternatively be at least about 0.005 sec, and can optionally be at least about 0.01 sec. In other aspects, the activation period can be up to a maximum of about 3 sec. The activation period can alternatively be up to about 2 sec, and can optionally be up to about 1.5 sec.

The activation chamber 304 can be a tuned chamber within which the electromagnetic energy can produce an operative standing wave. In a particular feature, the activation chamber 304 can be configured to be a resonant chamber. Examples of suitable arrangements for the resonant, activation chamber system are described in a U.S. Pat. No. 5,536,921 entitled SYSTEM FOR APPLYING MICROWAVE ENERGY IN SHEET-LIKE MATERIAL by Hedrick et al. which has an issue date of Jul. 16, 1996; and in U.S. Pat. No. 5,916,203 entitled COMPOSITE MATERIAL WITH ELASTICIZED PORTIONS AND A METHOD OF MAKING THE SAME by Brandon et al which has a issue date of Jun. 29, 1999. The entire disclosures of these documents are incorporated herein by reference in a manner that is consistent herewith. Another suitable activation system for activating the binder fibers is disclosed in co-assigned U.S. patent application Ser. No. 10/037,385, filed Dec. 20, 2001 and entitled Method and Apparatus for Making On-Line Stabilized Absorbent Materials.

The absorbent structure 101 exiting the activation chamber 304 can also be selectively cooled or otherwise processed following heating of the binder fibers. The cooling of the absorbent structure 101 may be provided by a cooling system that includes: chilled air, a refrigerated atmosphere, radiant cooling, transvector cooling, ambient air cooling, or the like, as well as combinations thereof. As representatively shown in FIG. 5, the cooling system may include a chilled-air supply hood 321, a vacuum conveyor 323, a blower 325 and a chiller or other refrigeration unit 327. The refrigeration unit 327 can provide a suitable coolant to a heat exchanger 329, and the blower can circulate air through the heat exchanger for cooling. The cooled air can be directed into the supply hood 321 and onto the absorbent structure 101. The air can then be drawn out of the hood 321 for recirculation through the heat exchanger 329.

In a particular aspect, the absorbent structure 101 can be cooled to a setting temperature which is below the melting temperature of the binder fiber material. In another aspect, the absorbent structure 101 can be cooled to a temperature of not more than a maximum of 200° C. within a selected setting distance downstream of the activation chamber 304. In a further feature, the absorbent structure 101 can be cooled to a temperature of not more than a maximum of 150° C. within the selected setting distance. Accordingly, the setting distance can be measured after ending the exposure of the absorbent structure 101 to the high-frequency electromagnetic energy in the activation chamber 304. In a particular feature, the setting distance can be a minimum of about 0.5 m. The setting distance can alternatively be at least a minimum of about 0.75 m, and can optionally be at least about 1 m. In another feature, the setting distance can be a maximum of not more than about 30 m. The setting distance can alternatively be not more than about 20 m, and can optionally be not more than about 10 m.

In another aspect, an incremental portion of the heated absorbent structure 101 may be cooled to the desired setting temperature within a distinctive setting period, as determined from the time that the incremental portion of the activated structure exits the activation chamber 304. Accordingly, the setting period can be measured after ending the exposure of the absorbent structure to the high-frequency electromagnetic energy in the activation chamber 304. In a particular feature, the setting period can be a minimum of about 0.05 sec. The setting period can alternatively be at least a minimum of about 0.075 sec, and can optionally be at least about 0.1 sec. In another feature, the setting period can be a maximum of not more than about 3 sec. The setting period can alternatively be not more than about 2 sec, and can optionally be not more than about 1 sec.

The temperature of the absorbent structure 101 can be determined by employing an infrared scanner, such as a model No. LS601RC60 available from Land Infrared, a business having offices located in Bristol, Pa., U.S.A. With this device, the temperature can be determined by aiming the measurement probe at the centerline of the structure 101, and setting up the probe (in accordance with the instruction manual) at a separation distance of 12 inches, as measured perpendicular to the structure. Alternatively, a substantially equivalent device may be employed.

The stabilized absorbent structure 101 may also be compressed (e.g., by subjecting the structure to a debulking operation) to provide a desired thickness and density to the stabilized absorbent structure. In a desired aspect, the debulking is conducted after the absorbent structure has been cooled. As representatively shown, the debulking operation can be provided by a pair of counter-rotating nip rollers 331. The debulking operation can alternatively be provided by a converging conveyor system, indexed platens, elliptical rollers, or the like, as well as combinations thereof.

In a particular aspect, the thickness of the absorbent structure following debulking can be a minimum of about 0.5 mm. The debulked thickness can alternatively be at least about 1 mm, and can optionally be at least about 2 mm. In another aspect, the debulked thickness can be up to a maximum of about 25 mm. The debulked thickness can alternatively be up to about 15 mm, and can optionally be up to about 10 mm.

In another aspect, the debulked stabilized absorbent structure 101 can have a density which is at least a minimum of about 0.05 g/cm$^3$. The debulked density can alternatively be at least about 0.08 g/cm$^3$, and can optionally be at least about 0.1 g/cm$^3$. In further aspects, the debulked density can be up to a maximum of about 0.5 g/cm$^3$, or more. The debulked density can alternatively be up to about 0.45 g/cm$^3$, and can optionally be up to about 0.4 g/cm$^3$.

In optional configurations, the stabilized absorbent structure 101 may be cut or otherwise divided to provide a desired lateral shaping (e.g., width profile) of the structure, and/or to provide a laterally contoured structure. The cutting system may, for example, include a die cutter, a water cutter, rotary knives, reciprocating knives or the like, as well as combinations thereof. The shaping may be conducted prior to and/or after the absorbent structure 101 is subjected to the activation of the binder fiber with the selected activation system 304.

Figure 13:
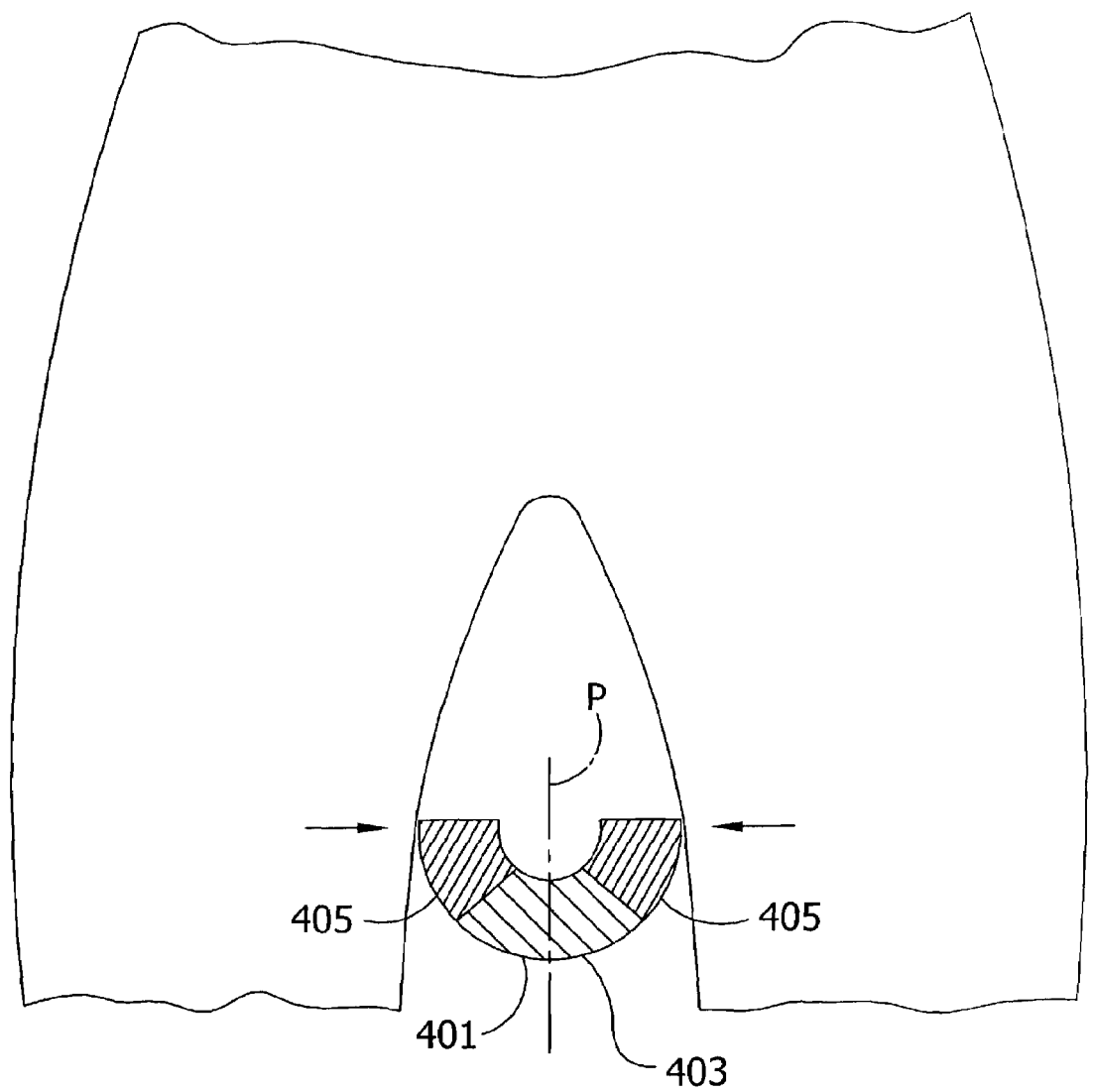
FIG. 13 is a cross-section of another embodiment of a stabilized absorbent structure of the present invention under lateral compression.
Figure 14:
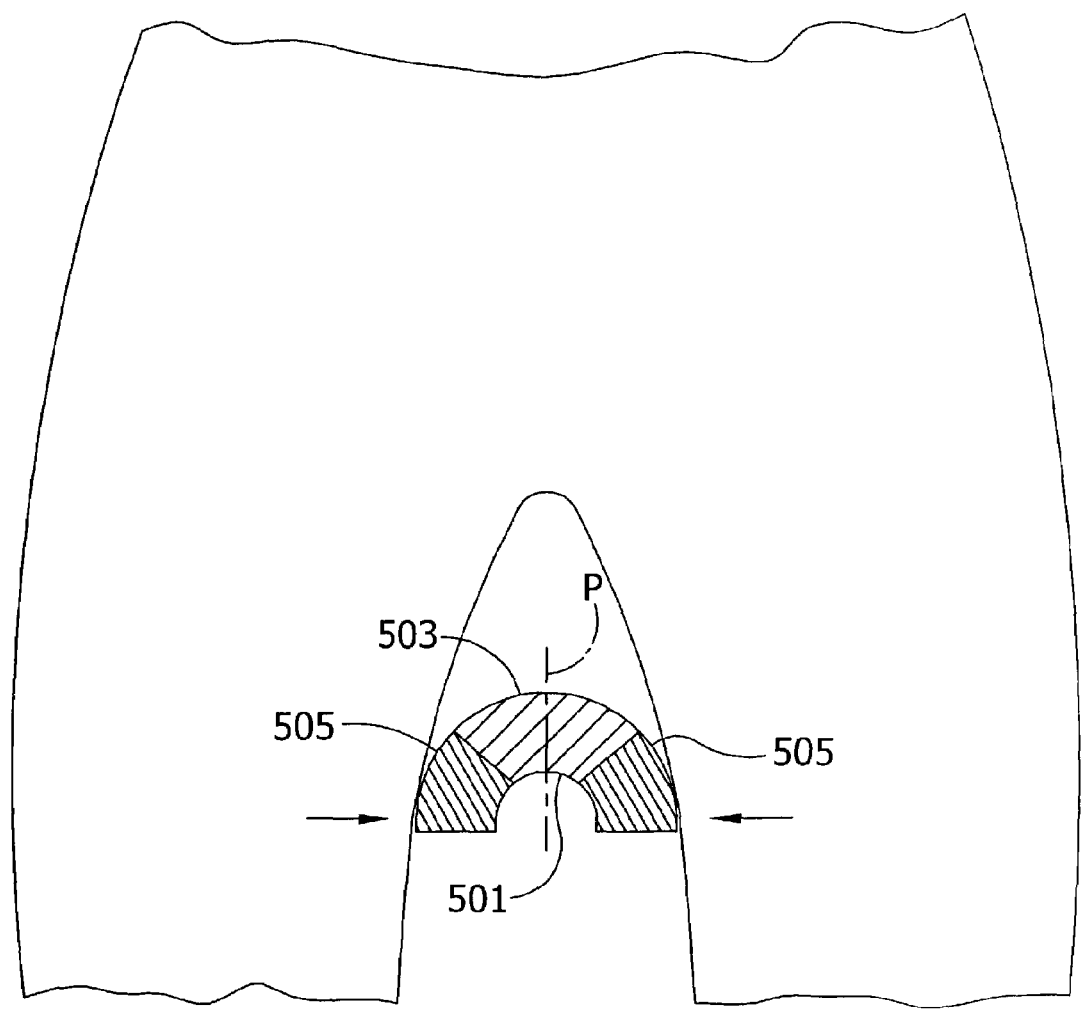
FIG. 14 is a cross-section of yet another embodiment of a stabilized absorbent structure under lateral compression.

FIGS. 13 and 14 schematically illustrate additional embodiments of stabilized absorbent structures 401 (FIG. 13), 501 (FIG. 14) having substantially the same construction as the stabilized absorbent structure 101. In each of these embodiments, the absorbent structure 401, 501 has a lateral compression stiffness that is non-uniform across the width of the absorbent structure, particularly at the longitudinal portion of the absorbent structure corresponding to the crotch region (e.g., as indicated at 27 in FIG. 1) of the absorbent article into which the absorbent structure is incorporated.

Lateral compression stiffness is the critical buckling stress of a given structure that is expressed as being proportional to $E/\lambda^2$ as described at pg. 484 of Handbook of Physical Testing of Paper (Vol. 1—Second Edition), by R. E. Mark, C. C. Habegar, J. Borche and M. B. Lynch (ISBN:0-8247-0498-3). Here, "E" is an intrinsic property of the structure referred to as the elastic modulus of the structure which is dependent on the "bond" points per unit volume within the structure. The bonds could be actual joints or various degrees of entanglements among fibers. The term "$\lambda$" is the slenderness ratio of the absorbent structure, which as a significant effect on the lateral compression stiffness as described in further detail later herein.

More particularly, the lateral compression stiffness gradient across the width of the absorbent structure 401, 501 is desirably such that under lateral compression applied to the sides of the absorbent structure (e.g. as indicated by the arrows in FIGS. 13 and 14), such as when the absorbent article incorporating the absorbent structure is squeezed between the legs of the wearer, the absorbent structure assumes a pre-determined or otherwise non-random buckled configuration that is generally a function of the lateral compression stiffness gradient of the absorbent structure. More desirably, the absorbent structure 401, 501 assumes a generally buckled, or folded configuration that is generally symmetric about a plane P (shown in phantom in FIGS. 13 and 14) normal to the absorbent structure and in which the longitudinal axis of the structure lies.

As used in reference to the buckled configurations assumed by the stabilized absorbent structures 401, 501 (or other stabilized absorbent structures described herein) under lateral compression thereof, the terms "pre-determined" and "non-random" refer to the intended assumption of a desired configuration as a result of an absorbent structure construction in which the assumed configuration is a result of an intended non-uniform lateral stiffness gradient within the absorbent structure (e.g., other than a gradient resulting from material and process tolerances inherent in making such absorbent structures). Otherwise stated, the configuration assumed by a particular absorbent structure is consistently repeatable in absorbent structures of similar construction, e.g., having a similar lateral compression stiffness gradient across the width of the absorbent structure.

One suitable method by which the lateral, or edgewise compression stiffness can be determined is as follows. The weight of the absorbent structure is determined and then the thickness of the material is determined under a 0.2 psi (1.38 KPa) load. The absorbent structure is formed into a cylinder by bringing the longitudinal ends together. The ends may even be slightly overlapped, e.g., by up to 0.125 inches (3.18 mm). The ends are then stapled together with three staples. One staple is near the longitudinal axis of the absorbent structure, and the other two are adjacent the side edges of the absorbent structure. The longer dimension of the staple is desirably oriented about the circumference of the formed cylinder to minimize the effect of the staples on the testing. The cylinder is laid on one side edge of the absorbent structure, so that cylinder has a height corresponding to the width of the absorbent structure.

A detailed discussion of lateral, or edge-wise compression strength is given in The Handbook Of Physical And Mechanical Testing Of Paper And Paperboard, Richard E. Mark, editor, Dekker 1983, (Vol. 1). Based on theoretical models governing buckling stresses, in the edge-wise compression configuration described, the buckling stress (e.g., the critical buckling stress described previously) is proportional to $E*t^2/(H^2)$ with the proportionality constant being a function of $H^2/(R*t)$ where E is the Elastic modulus of the absorbent structure, H is the height of the cylinder (e.g., the width of the structure), R is the radius of the cylinder, and t is the thickness of the absorbent structure. Expressing the buckling stress in terms of force per basis weight, it can be shown that the parameter that needs to be maintained constant among different absorbent structures tested is $H^2/R$. For example, the length and width of the absorbent structure tested are desirably such that $H^2/R$ for the formed cylinder is about 2.1 inches (5.3 cm).

An INSTRON tester, or similar instrument is configured with a bottom platform, a platen larger than the circumference of the specimen to be tested and parallel to the bottom platform, attached to a compression load cell placed in the inverted position. The specimen is placed on the platform, under the platen. The platen is then brought into contact with the specimen and compresses the specimen at a rate of about 25 mm/min. The maximum force (e.g., the lateral compression stiffness) obtained in compressing the specimen to 50% of its width is recorded. If the material buckles, it is typical for the maximum force to be reached before the sample is compressed to 50%. As an additional example, U.S. Pat. No. 6,214,274 to Melius et al. discloses a suitable lateral, or edgewise, compression test and is hereby incorporated by reference to the extent that it is consistent herewith.

In the illustrated embodiment of FIG. 13, the lateral compression stiffness of the absorbent structure 401 substantially decreases laterally outward from the longitudinal axis of the absorbent structure toward the side edges thereof. More particularly, a laterally central region 403 of the absorbent structure 401 has a lateral compression stiffness that is substantially greater than the lateral compression stiffness of laterally opposite side regions 405 extending outward from the central region to the side edges of the absorbent structure. The lines shown in FIG. 13 dividing the central region 403 from the laterally opposite side regions 405 are solely for the purpose of illustrating the present invention and are not intended to indicate the presence of individual structures adhered together in side-by-side relationship to form the absorbent structure 401. Rather, it is desired that the absorbent structure 401 be of unitary construction similar to the absorbent structure 101.

As an example, the lateral compression stiffness of the absorbent structure 401 at the longitudinal axis, such as within the laterally central region 403, is desirably in the range of about 2 to about ten times greater than the lateral compression stiffness adjacent the side edges of the structure, such as within the lateral side regions 405 of the structure.

The lateral compression stiffness of the absorbent structure 401 is generally a function of the basis weight of the absorbent structure across its width. For example, where the basis weight is non-uniform across the width of the absorbent structure and the density is generally uniform, the thickness of the absorbent structure is also non-uniform across the width of the structure, such as shown in FIG. 2 for the absorbent structure 101 as well as in FIGS. 18a and 18b, and 19a and 19b as described later herein. In such an embodiment, the basis weight at the longitudinal axis of the absorbent structure, such as in the laterally central region 403 thereof, is substantially greater than the basis weight adjacent the side edges, such as in the lateral side regions 405 of the absorbent structure. Likewise, the thickness at the longitudinal axis of the absorbent structure, such as in the laterally central region 403 thereof, is substantially greater than the thickness adjacent the side edges, such as in the lateral side regions 405 of the absorbent structure. The increased thickness results in a greater lateral compression stiffness at the longitudinal axis of the absorbent structure.

More particularly, and without being bound to a particular theory, it is believed that where the density is generally uniform across the width of the absorbent structure and the basis weight is non-uniform, the lateral compression stiffness is more particularly a function of the slenderness ratio "λ" of the absorbent structure. The slenderness ratio λ is generally defined by the following equation:

$$\lambda = \frac{L}{[M/A]^{0.5}}$$

where,

L is the width of the absorbent structure generally at the longitudinal position at which the lateral compression is applied to the structure (e.g., as measured in the direction of compression);

M is the moment of inertia of the absorbent structure in the cross-sectional plane of the absorbent structure at the longitudinal position of lateral compression; and A is the cross-sectional area of the absorbent structure at the longitudinal position of lateral compression.

More broadly stated, the slenderness ratio λ is generally proportional to L/t, where L is the length of the absorbent structure at the longitudinal position of lateral compression (e.g., as measured in the direction of compression) and t is the thickness of the absorbent structure across the absorbent structure at the longitudinal position of lateral compression. The lateral compression stiffness in this instance is proportional to the inverse square of the slenderness ratio λ (i.e., $1/\lambda^2$). Thus, in regions of greater thickness across the width of the absorbent structure, the slenderness ratio λ decreases, thereby increasing the lateral compression stiffness at the regions of increased thickness. In contrast, in regions where the thickness of the absorbent structure decreases, the slenderness ratio correspondingly increases, thereby decreasing the lateral compression stiffness at the regions of decreased thickness.

For the absorbent structure 401 of FIG. 13, the slenderness ratio λ is desirably non-uniform across the width of the absorbent structure, and more desirably the slenderness ratio is lower at the longitudinal axis (e.g., within the laterally central region 403) of the absorbent structure than the slenderness ratio adjacent the side edges thereof (e.g., within the side regions 405 of the absorbent structure.

Alternatively, or additionally, the density at the longitudinal axis of the absorbent structure 401, such as in the laterally central region 403 thereof, can be substantially greater than the density adjacent the side edges, such as in the laterally opposite side regions 405 of the absorbent structure. For example, where the basis weight is non-uniform across the width of the structure 401 and the thickness is substantially uniform, then the density is non-uniform across the width of the structure, with the region of higher density (e.g., the laterally central region 403 in the illustrated embodiment) corresponding to the region of higher basis weight. The greater density, such as at the longitudinal axis (e.g., within the laterally central region 403) thereby corresponds to a greater lateral compression stiffness within that region.

Figure 18A:
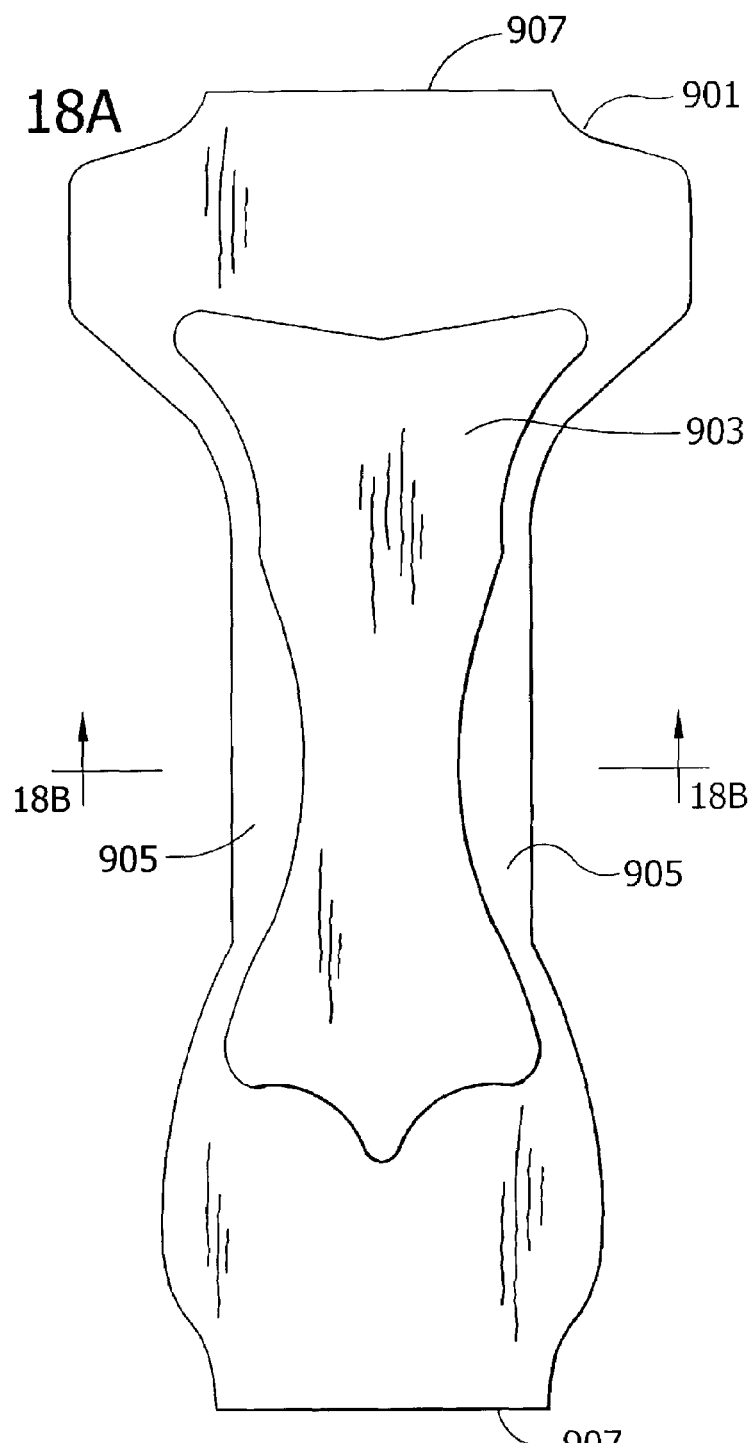
FIG. 18a is a top plan view of another embodiment of a stabilized absorbent structure of the present invention.
Figure 18B:
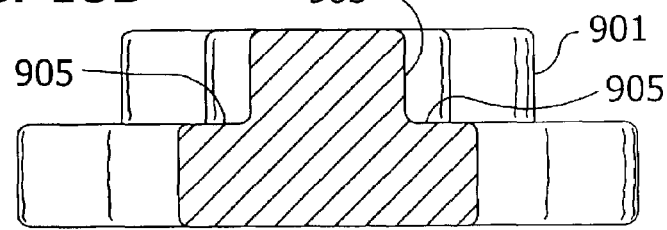
Figure 19A:
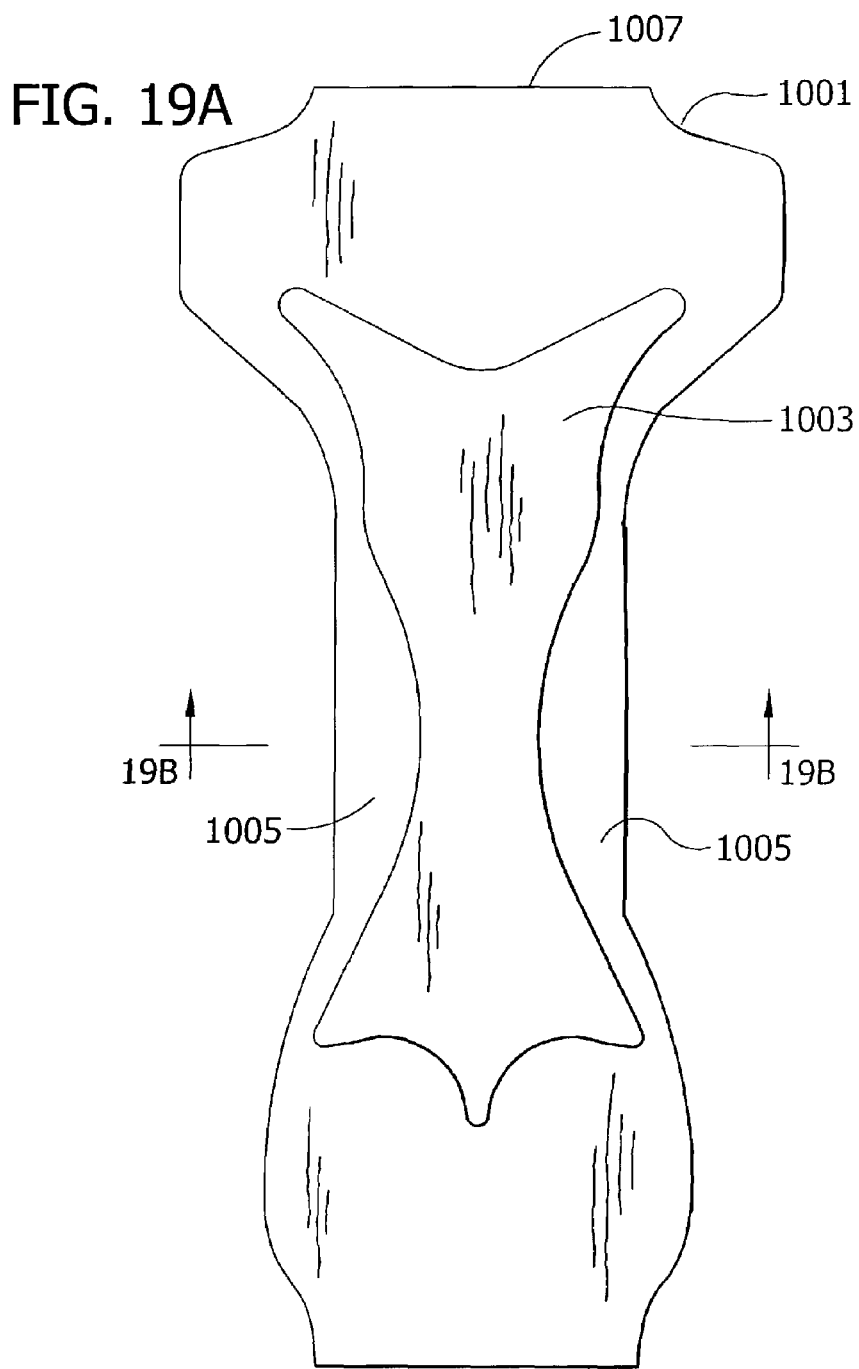
FIG. 19a is a top plan view of another embodiment of a stabilized absorbent structure of the present invention.
Figure 19B:
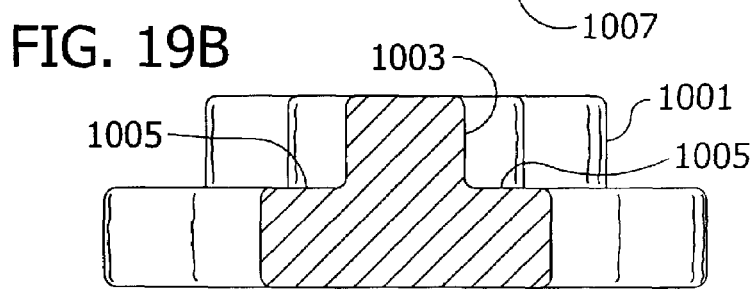

In use, an absorbent article, such as the diaper 21 shown in FIG. 1, incorporating the absorbent structure 401, such as the absorbent structure 101 of FIG. 2 or the absorbent structures 901, 1001 respectively shown in FIGS. 18a and 19a, is placed on the wearer in a conventional manner. The schematic illustration of FIG. 13 includes only the absorbent structure 401, e.g., removed from the diaper 21, to better illustrate the configuration of the absorbent structure during lateral compression of the diaper. When lateral compression is applied to the diaper 21 by the wearer, such as by being squeezed between the wearer's legs as shown in FIG. 13, the lateral compression stiffness gradient of the absorbent structure 401 results in the absorbent structure assuming a generally arcuate configuration that is generally symmetric about the normal plane of the absorbent structure.

More particularly, as shown in FIG. 13, the absorbent structure 401 assumes a configuration that is generally concave relative to the wearer. That is, the longitudinal axis, or laterally central region 403 of the absorbent structure 401, is spaced further away from the wearer than the side edges, or laterally opposite side regions 405, of the absorbent structure. Such a configuration provides a basin-like function that retains surges of liquid body waste until the absorbent body (e.g., the absorbent body 53 of FIG. 2) can absorb the waste.

The absorbent structure 501 of FIG. 14 has a lateral compression stiffness gradient that is substantially the opposite of the stiffness gradient of the absorbent structure 401 of FIG. 13. That is, the lateral compression stiffness of the absorbent structure 501 substantially increases laterally outward from the longitudinal axis of the absorbent structure toward the side edges thereof. More particularly, the laterally central region 503 of the absorbent structure 501 has a lateral compression stiffness that is substantially greater than the lateral compression stiffness at the laterally opposite side regions 505 of the absorbent structure.

The lateral compression stiffness of the absorbent structure 501 adjacent its side edges, e.g., within each of the laterally opposite side regions 505, is desirably at least about two to ten times greater than the stiffness generally at the longitudinal axis of the absorbent structure, e.g., within the laterally central region 503 thereof.

Where the density is generally uniform across the width of the absorbent structure 501, the slenderness ratio λ is desirably non-uniform across the width of the absorbent structure, and more desirably the slenderness ratio is greater at the longitudinal axis (e.g., within the laterally central region 503) of the absorbent structure than the slenderness ratio adjacent the side edges thereof (e.g., within the side regions 505 of the absorbent structure.

In use, an absorbent article, such as the diaper 21 shown in FIG. 1, incorporating the absorbent article 501 is placed on the wearer in a conventional manner. The schematic illustration of FIG. 14 includes only the absorbent structure 501, e.g., removed from the diaper 21, to better illustrate the configuration of the absorbent structure during lateral compression of the diaper. When lateral compression is applied to the diaper 21 by the wearer, such as by being squeezed between the wearer's legs as shown in FIG. 14, the lateral compression stiffness gradient of the absorbent structure 501 results in the absorbent structure assuming a generally arcuate configuration that is generally symmetric about the plane P of the absorbent structure. More particularly, as shown in FIG. 14, the absorbent structure 501 assumes a generally buckled configuration that is generally convex relative to the wearer's crotch. That is, the longitudinal axis, or laterally central region 503 of the absorbent structure 501, is nearer to the crotch of the wearer than the side edges, or laterally opposite side regions 505, of the absorbent structure.

Figure 15:
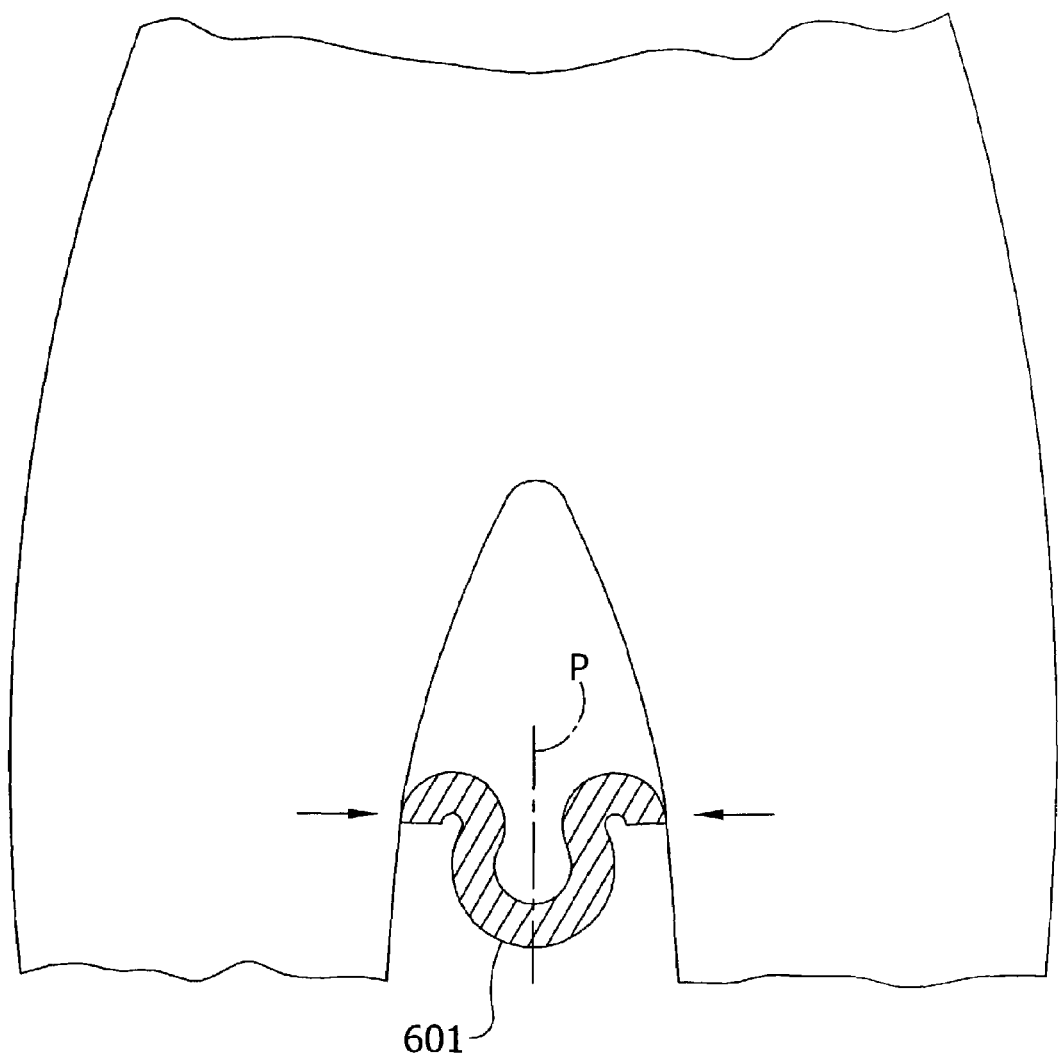
FIG. 15 is a cross-section of another embodiment of a stabilized absorbent structure under lateral compression.
Figure 16:
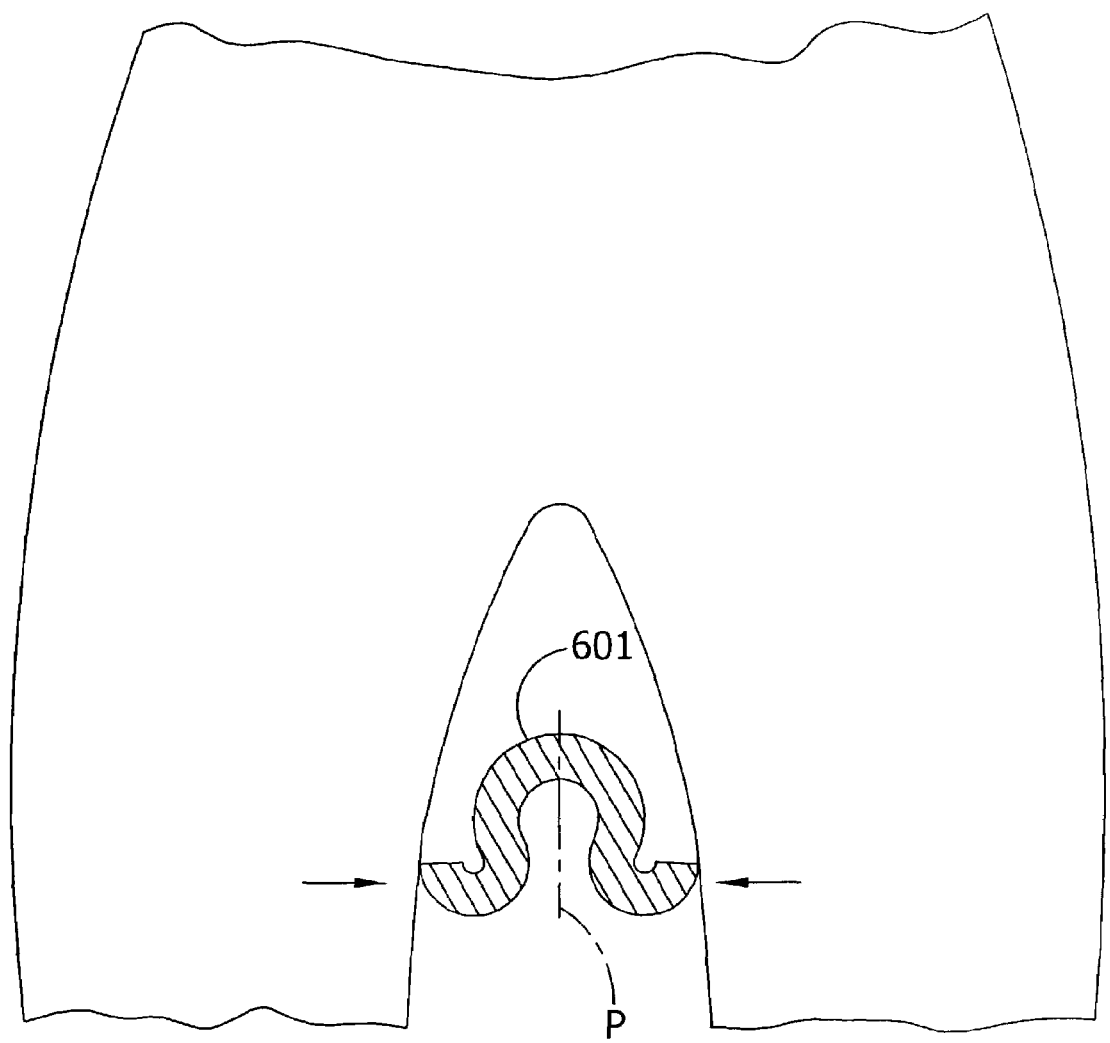
FIG. 16 is a cross-section of still another embodiment of a stabilized absorbent structure under lateral compression.

It is contemplated that the absorbent structure 401, 501 may also assume a pre-determined buckled, or folded configuration other than the generally arcuate configurations illustrated in FIGS. 13 and 14. For example, as shown in FIGS. 15 and 16, the absorbent structure 601 (FIG. 15), 701 (FIG. 16) may have a lateral compression stiffness gradient across the width of the absorbent structure such that the absorbent structure assumes a generally "M" or inverted "W" or inverted "Ω" configuration (FIG. 15) under lateral compression, or it may be such that it assumes a generally "W" or "Ω" configuration (FIG. 16) under lateral compression.

Figure 17A:
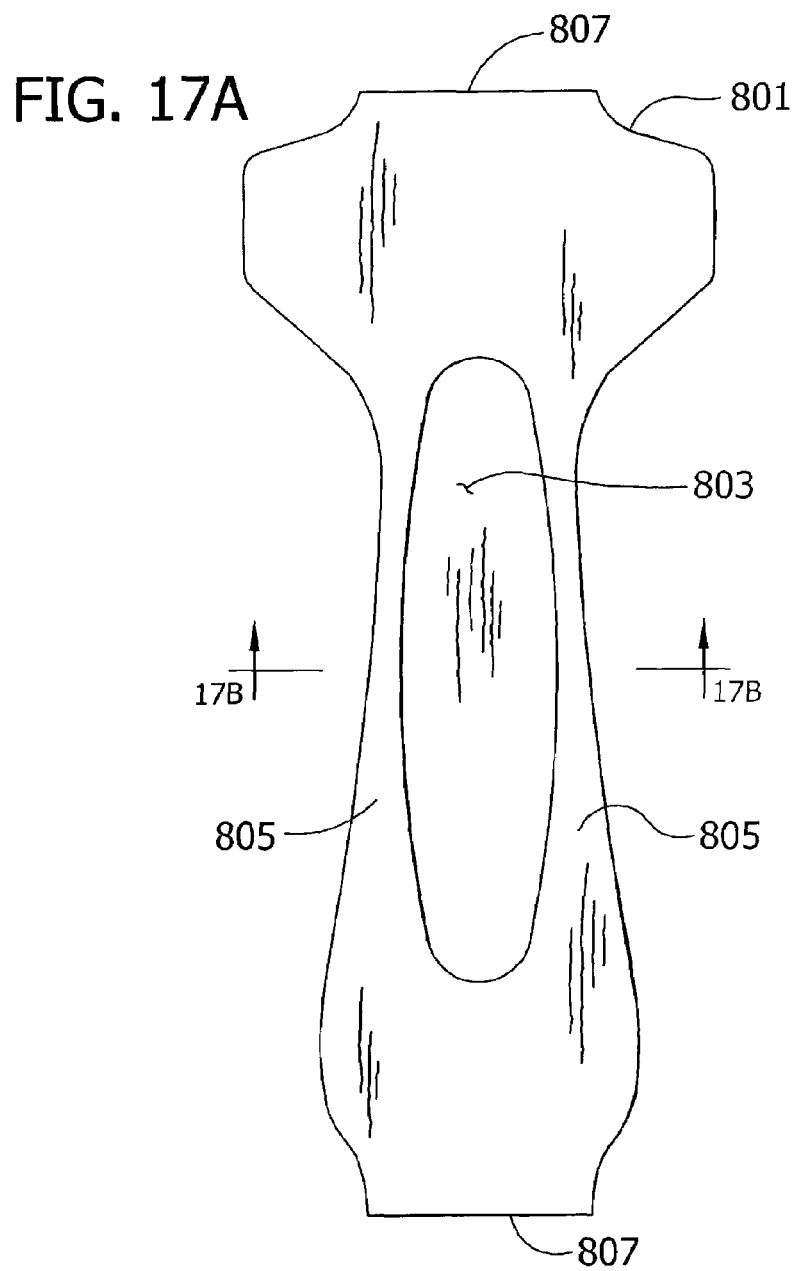
FIG. 17a is a top plan view of another embodiment of a stabilized absorbent structure of the present invention.
Figure 17B:
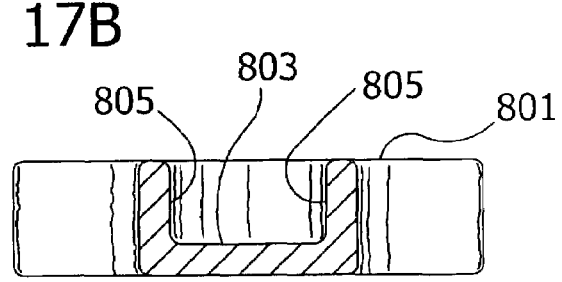

As a further example, FIGS. 17a and 17b illustrate one absorbent structure 801 constructed in accordance with the present invention that will assume a generally "Ω" configuration under lateral compression. The absorbent structure 801 has an ovate, laterally centrally disposed void, or "bucket" region 803 in which the basis weight is substantially less than the basis weight of the absorbent structure between the bucket region and the laterally opposite side edges, or side regions 805, of the absorbent structure. The density is generally uniform across the width of the absorbent structure 801. As such, the slenderness ratio $\lambda$ is substantially greater in the bucket region 803 than in the side regions 805. Consequently, the lateral compression stiffness of the absorbent structure is substantially lower in the bucket region than at the side regions, thereby resulting in the absorbent structure assuming the generally Ω configuration shown in FIG. 16.

As is also shown in FIG. 17a, the slenderness ratio of the absorbent structure is also non-uniform along the length of the absorbent structure. For example, the slenderness ratio of the absorbent structure at longitudinal end regions 807, e.g., longitudinally beyond the bucket region 803, is substantially lower than the slenderness ratio within the bucket region due to the increased thickness relative to the thickness of the absorbent structure within the bucket region. Consequently, the lateral compression stiffness of the absorbent structure increases toward the longitudinal end regions 807 of the absorbent structure.

FIGS. 18a, and 18b, and FIGS. 19a and 19b respectively illustrate stabilized absorbent structures 901, 1001, having a laterally central region 903, 1003, in which the thickness is greater than the thickness of the absorbent structure at laterally opposite side regions 905, 1005 thereof. The density is generally uniform across the width of each of the absorbent structures 901, 1001. As such, the slenderness ratio $\lambda$ of each structure is substantially lower in the laterally central region 903, 1003 than in the side regions 905, 1005. Consequently, the lateral compression stiffness of the absorbent structure is substantially greater at the central region 903, 1003 than at the side regions 905, 1005, thereby resulting in the absorbent structure assuming the generally concave configurations shown in FIGS. 13 and 15.

As is also shown in FIGS. 18a and 19a, the slenderness ratio of each of the absorbent structures 901, 1001 is also non-uniform along the length of each absorbent structure. For example, the thickness of the absorbent structure at longitudinal end regions 907, 1007 thereof is substantially lower than at the central region 903, 1003. Therefore, the slenderness ratio increases toward the longitudinal end regions 907, 1007, thereby decreasing the lateral compression stiffness of the absorbent structure toward the longitudinal end regions thereof.

It is further contemplated that other pre-determined buckled configurations of the absorbent structure can be achieved under lateral compression thereof depending on the stiffness gradient across the width of the absorbent structure without departing from the scope of this invention. It is also understood that the pre-determined configuration assumed by the absorbent structure need not be symmetric about the plane P in which the longitudinal axis of the structure lies, as long as the pre-determined configuration can be consistently repeated from one absorbent structure to another.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article comprising:
   a liner adapted for contiguous relationship with the wearer's body;
   an outer cover in generally opposed relationship with the liner; and
   an absorbent body disposed between the liner and the outer cover, the absorbent body at least partially comprising an absorbent structure having a length, a thickness, a width, a longitudinal axis, laterally opposite side edges and a non-uniform lateral compression stiffness across its width, said non-uniform lateral compression stiffness being such that the absorbent structure assumes a generally buckled configuration under lateral compression thereof, said buckled configuration of the absorbent structure being generally symmetric about a plane normal to the absorbent structure and in which the longitudinal axis of the absorbent structure lies, the lateral compression stiffness of the absorbent structure generally decreasing laterally outward from the longitudinal axis thereof toward the side edges of the absorbent structure.

2. An absorbent article as set forth in claim 1 wherein the non-uniform lateral compression stiffness across the width of the absorbent structure is such that the absorbent structure assumes a generally arcuate configuration under lateral compression thereof whereby the absorbent structure is nearer to the wearer at the opposite side edges of the absorbent structure than at the longitudinal axis thereof.

3. An absorbent article as set forth in claim 1 wherein the absorbent structure has a first lateral compression stiffness generally at the longitudinal axis and a second lateral compression stiffness adjacent each of the laterally opposite side edges, the first lateral compression stiffness being about two to about ten times greater than the second lateral compression stiffness.

4. An absorbent article comprising:
a liner adapted for contiguous relationship with the wearer's body;
an outer cover in generally opposed relationship with the liner; and
an absorbent body disposed between the liner and the outer cover, the absorbent body at least partially comprising an absorbent structure having a length, a thickness, a width, a longitudinal axis, and a non-uniform lateral compression stiffness across its width, said non-uniform lateral compression stiffness being such that the absorbent structure assumes a generally buckled configuration under lateral compression thereof, said buckled configuration of the absorbent structure being generally symmetric about a plane normal to the absorbent structure and in which the longitudinal axis of the absorbent structure lies, the absorbent structure having a generally uniform density across the width of the absorbent structure along at least a longitudinal portion of the absorbent structure, wherein the absorbent structure has laterally opposite side edges, the lateral compression stiffness of the absorbent structure generally increasing laterally outward from the longitudinal axis toward the side edges of the absorbent structure.

5. An absorbent article as set forth in claim 1 wherein the absorbent structure comprises absorbent fibers and binder fibers activated to form inter-fiber bonds within the absorbent structure.

6. An absorbent article as set forth in claim 5 wherein the binder fibers are multi-component fibers whereby at least one binder fiber component has a melting temperature that is less than a melting temperature of at least one other binder fiber component.

7. An absorbent article as set forth in claim 5 wherein the absorbent structure is of unitary construction.

8. An absorbent article as set forth in claim 1 wherein the absorbent structure has a basis weight that is non-uniform across the width of the absorbent structure.

9. An absorbent article as set forth in claim 8 wherein the basis weight of the absorbent structure decreases laterally outward from the longitudinal axis toward the side edges of the absorbent structure.

10. An absorbent article as set forth in claim 4 wherein the absorbent structure has a basis weight that increases laterally outward from the longitudinal axis toward the side edges of the absorbent structure.

11. An absorbent article as set forth in claim 1 wherein the absorbent structure has a density that is non-uniform across the width of the absorbent structure.

12. An absorbent article as set forth in claim 11 wherein the density of the absorbent structure generally decreases laterally outward from the longitudinal axis toward the side edges of the absorbent structure.

13. An absorbent article as set forth in claim 1 wherein the absorbent structure has a thickness that is non-uniform across the width of the absorbent structure.

14. An absorbent article as set forth in claim 13 wherein the thickness of the absorbent structure generally decreases laterally outward from the longitudinal axis toward the side edges of the absorbent structure.

15. An absorbent article as set forth in claim 4 wherein the absorbent structure has a thickness that generally increases laterally outward from the longitudinal axis toward the side edges of the absorbent structure.

16. An absorbent article as set forth in claim 5 wherein the concentration of binder fibers in the absorbent structure is non-uniform along at least one of the length, the width and the thickness of the absorbent structure.

17. An absorbent article as set forth in claim 1 wherein the width of the absorbent structure is non-uniform along the length of the absorbent structure.

18. An absorbent article as set forth in claim 1 wherein the generally buckled configuration is at least one of an M configuration, a generally inverted "W" configuration and a generally inverted "Ω" configuration.

19. An absorbent article as set forth in claim 4 wherein the generally buckled configuration is at least one of a generally "W" configuration and a generally "Ω" configuration.

20. An absorbent article as set forth in claim 4 wherein the absorbent structure has an upper surface, and a generally laterally central bucket region formed in the upper surface, wherein the thickness of the absorbent structure within the bucket region is substantially less than the thickness of the absorbent structure laterally between the bucket region and the side edges of the absorbent structure.

21. An absorbent article as set forth in claim 20 wherein the bucket region is generally ovate.

22. An absorbent article as set forth in claim 1 wherein the absorbent structure has a slenderness ratio that is generally non-uniform across the width of the absorbent structure.

23. An absorbent article as set forth in claim 22 wherein the slenderness ratio of the absorbent structure generally decreases laterally outward from the longitudinal axis toward the side edges of the absorbent structure.

24. An absorbent article as set forth in claim 4 wherein the absorbent structure has a slenderness ratio that generally increases laterally outward from the longitudinal axis toward the side edges of the absorbent structure.

25. An absorbent article as set forth in claim 22 wherein the slenderness ratio of the absorbent structure is also non-uniform along the length of the absorbent structure.

26. An absorbent article comprising:
a liner adapted for contiguous relationship with the wearer's body;
an outer cover in generally opposed relationship with the liner; and
an absorbent body disposed between the liner and the outer cover, the absorbent body at least partially comprising an absorbent structure having a length, a thickness, a width, a longitudinal axis, laterally opposite side edges and a non-uniform lateral compression stiffness across its width, said stiffness gradient being such that the absorbent structure assumes a pre-determined generally buckled configuration under lateral compression thereof, the lateral compression stiffness of the absorbent structure generally decreasing laterally outward from the longitudinal axis thereof toward the side edges of the absorbent structure.

27. An absorbent article as set forth in claim 26 wherein said pre-determined configuration assumed by the absorbent structure under lateral compression thereof is generally symmetric about a plane normal to the absorbent structure and in which the longitudinal axis of the absorbent structure lies.

28. An absorbent article as set forth in claim 27 wherein the absorbent structure assumes a generally arcuate configuration under lateral compression.

29. An absorbent article as set forth in claim 27 wherein the absorbent structure assumes at least one of an M configuration, a generally inverted "W" configuration and a generally inverted "Ω" configuration under lateral compression thereof.

30. An absorbent article comprising:
a liner adapted for contiguous relationship with the wearer's body;
an outer cover in generally opposed relationship with the liner; and
an absorbent body disposed between the liner and the outer cover, the absorbent body at least partially comprising an absorbent structure having a length, a thickness, a width, a longitudinal axis, laterally opposite side edges and a non-uniform lateral compression stiffness across its width, said stiffness gradient being such that the absorbent structure assumes a non-random generally buckled configuration under lateral compression thereof, the lateral compression stiffness of the absorbent structure generally decreasing laterally outward from the longitudinal axis thereof toward the side edges of the absorbent structure.

31. An absorbent article as set forth in claim 30 wherein said non-random configuration assumed by the absorbent structure under lateral compression thereof is generally symmetric about a plane normal to the absorbent structure and in which the longitudinal axis of the absorbent structure lies.

32. An absorbent article as set forth in claim 31 wherein the absorbent structure assumes a generally arcuate configuration under lateral compression.

33. An absorbent article as set forth in claim 31 wherein the absorbent structure assumes at least one of an M configuration, a generally inverted "W" configuration and a generally inverted "Ω" configuration under lateral compression thereof.

* * * * *

UNITED STATES PATENT AND TRADEMARK OFFICE
CERTIFICATE OF CORRECTION

PATENT NO. : 7,732,039 B2
APPLICATION NO. : 10/306277
DATED : June 8, 2010
INVENTOR(S) : Jayant Chakravarty et al.

It is certified that error appears in the above-identified patent and that said Letters Patent is hereby corrected as shown below:

Column 10, line 10, between "of" and "River" insert -- High --

Signed and Sealed this
Fourth Day of January, 2011

David J. Kappos
*Director of the United States Patent and Trademark Office*